(12) United States Patent
Oba et al.

(10) Patent No.: US 9,103,717 B2
(45) Date of Patent: Aug. 11, 2015

(54) OPTICAL SENSOR AND IMAGE FORMING APPARATUS CONFIGURED TO DETECT INSIDE DIFFUSELY-REFLECTED LIGHT

(71) Applicants: Yoshihiro Oba, Miyagi (JP); Satoru Sugawara, Miyagi (JP); Toshihiro Ishii, Miyagi (JP); Fumikazu Hoshi, Miyagi (JP)

(72) Inventors: Yoshihiro Oba, Miyagi (JP); Satoru Sugawara, Miyagi (JP); Toshihiro Ishii, Miyagi (JP); Fumikazu Hoshi, Miyagi (JP)

(73) Assignee: RICOH COMPANY, LTD., Tokyo (JP)

( * ) Notice: Subject to any disclaimer, the term of this patent is extended or adjusted under 35 U.S.C. 154(b) by 181 days.

(21) Appl. No.: 13/779,949

(22) Filed: Feb. 28, 2013

(65) Prior Publication Data

US 2013/0228674 A1 Sep. 5, 2013

(30) Foreign Application Priority Data

Mar. 1, 2012 (JP) .................................. 2012-044930

(51) Int. Cl.
*G01J 4/00* (2006.01)
*G01J 1/04* (2006.01)
*G01N 21/21* (2006.01)
*G01N 21/55* (2014.01)
*G01N 21/57* (2006.01)

(52) U.S. Cl.
CPC ................ *G01J 1/0429* (2013.01); *G01N 21/21* (2013.01); *G01N 21/55* (2013.01); *G01N 21/57* (2013.01); *G01N 2021/556* (2013.01)

(58) Field of Classification Search
CPC .................. G03G 15/5029; G03B 2215/00751
USPC .............. 399/45; 356/369, 445–448; 250/216
See application file for complete search history.

(56) References Cited

U.S. PATENT DOCUMENTS

| 5,835,220 A | * | 11/1998 | Kazama et al. ................ 356/369 |
| 6,499,732 B1 | * | 12/2002 | Akaba .......................... 271/9.09 |
| 6,731,886 B2 | | 5/2004 | Takeda |
| 7,978,739 B2 | | 7/2011 | Sugawara et al. |
| 8,035,676 B2 | | 10/2011 | Harasaka et al. |
| 8,111,725 B2 | | 2/2012 | Ishii et al. |
| 2004/0162692 A1 | * | 8/2004 | Ye et al. ........................ 702/117 |
| 2009/0295902 A1 | | 12/2009 | Sato et al. |
| 2010/0328747 A1 | | 12/2010 | Jikutani et al. |
| 2011/0037825 A1 | | 2/2011 | Jikutani et al. |

(Continued)

FOREIGN PATENT DOCUMENTS

| JP | 10-160687 | 6/1998 |
| JP | 11-249353 | 9/1999 |

(Continued)

*Primary Examiner* — Renee D Chavez
(74) *Attorney, Agent, or Firm* — Cooper & Dunham LLP

(57) ABSTRACT

An optical sensor includes an irradiation system emitting linearly polarized light of a first polarization direction toward a surface of an object from an incident direction inclined with respect to a normal to the surface; a first light detection system including a first light detector placed on a light path of light emitted from the irradiation system and specularly reflected by the object; and a second light detection system including a separation optical element placed on a light path of light diffusely reflected by the object, on a plane of incidence of the object, and extracting a linearly polarized light component of the first polarization direction included in the light diffusely reflected by the object, a second light detector receiving the linearly polarized light component of the first polarization direction extracted by the separation optical element and a third light detector receiving the light diffusely reflected by the object.

9 Claims, 30 Drawing Sheets

(56) References Cited

U.S. PATENT DOCUMENTS

| | | |
|---|---|---|
| 2011/0109713 A1 | 5/2011 | Yamaguchi et al. |
| 2011/0115872 A1 | 5/2011 | Harasaka et al. |
| 2011/0170155 A1 | 7/2011 | Jikutani et al. |
| 2011/0211869 A1 | 9/2011 | Shouji et al. |
| 2011/0228035 A1 | 9/2011 | Ishii et al. |
| 2011/0261139 A1 | 10/2011 | Hoshi et al. |
| 2011/0267415 A1 | 11/2011 | Ohba et al. |
| 2012/0121297 A1 | 5/2012 | Jikutani et al. |
| 2012/0134693 A1 | 5/2012 | Hoshi et al. |

FOREIGN PATENT DOCUMENTS

| | | |
|---|---|---|
| JP | 2002-340518 | 11/2002 |
| JP | 2003-292170 | 10/2003 |
| JP | 2005-156380 | 6/2005 |
| JP | 2006-062842 | 3/2006 |
| JP | 2008-249714 | 10/2008 |
| WO | 2011/078196 A1 | 6/2011 |

* cited by examiner

OPTICAL SENSOR AND IMAGE FORMING APPARATUS CONFIGURED TO DETECT INSIDE DIFFUSELY-REFLECTED LIGHT

BACKGROUND OF THE INVENTION

1. Field of the Invention

The present invention relates to an optical sensor and an image forming apparatus, and in particular, to an optical sensor suitable for identifying an object, and an information processing apparatus including the optical sensor.

2. Description of the Related Art

An image forming apparatus such as a digital copier, a laser printer or the like transfers a toner image onto a surface of a recording medium typified by printing paper, fixes the toner image by heating and pressing it under predetermined conditions and thus forms an image. What is to take into consideration are conditions of a heating amount and/or a pressure during the fixing process, and in particular, in order to carry out image forming of high quality, it is necessary to set fixing conditions separately for each recording medium.

This is because image quality on a recording medium greatly depends on the material, thickness, humidity, smoothness, coated state and so forth. For example, concerning smoothness, a fixing rate may be degraded at dented parts of an uneven surface of printing paper depending on fixing conditions. Then, color heterogeneity may occur unless fixing is carried out under proper conditions suitable for a recording medium.

As recently image forming apparatuses have been advancing and expression methods have been diversifying, there are hundreds or more of types of recording media only for printing paper, and further, for each one of respective types, there are a wide variety of brands depending on specifications such as weights, thicknesses and so forth. For forming an image of high quality, it is necessary to finely set fixing conditions for each one of these brands.

Further, recently, the number of the brands has been increasing also for plain paper, coated paper typified by gloss coated paper, matt coated paper and art coated paper, plastic sheets and special paper with emboss effect on the surface thereof.

In a current image forming apparatus, a user himself or herself should set fixing conditions. Thus, there is troublesomeness such that the user is required to have knowledge for identifying the type of paper, and also, the user himself or herself should input setting contents according to the type of paper each time. Then, if the user makes a mistake concerning the setting contents, the user cannot obtain an optimum image.

Patent Reference No. 1 (Japanese Laid-Open Patent Application No. 2002-340518) discloses a surface nature identification apparatus including a sensor for identifying the surface nature of a recording material surface by coming into contact and scanning it.

Patent Reference No. 2 (Japanese Laid-Open Patent Application No. 2003-292170) discloses a printing apparatus identifying the type of paper using a pressure value detected from a pressure sensor coming into contact with the paper.

Patent Reference No. 3 (Japanese Laid-Open Patent Application No. 2005-156380) discloses a recording material identification apparatus identifying the type of a recording material using reflected light and transmitted light.

Patent Reference No. 4 (Japanese Laid-Open Patent Application No. 10-160687) discloses a sheet material identification apparatus identifying the material of a moving sheet material based on a reflected light amount reflected from a surface of the sheet material and a transmitted light amount transmitted by the sheet material.

Patent Reference No. 5 (Japanese Laid-Open Patent Application No. 2006-062842) discloses an image forming apparatus having a determination part that determines whether there is recording material contained in a paper supply part and whether there is the paper supply part, based on a detection output from a reflective optical sensor.

Patent Reference No. 6 (Japanese Laid-Open Patent Application No. 11-249353) discloses an image forming apparatus determining the surface nature of a recording medium upon emitting light to the recording medium and detecting respective light amounts of two polarization components of reflected light from the recording medium.

However, it may be difficult to identify an object in detail without much increasing the apparatus cost and/or size.

SUMMARY OF THE INVENTION

An optical sensor according to one aspect of the present invention includes an irradiation system emitting linearly polarized light of a first polarization direction toward a surface of an object from an incident direction inclined with respect to a direction of a normal to the surface; a first light detection system including a first light detector placed on a light path of light emitted from the irradiation system and specularly reflected by the object; and a second light detection system that includes a separation optical element placed on a light path of light diffusely reflected by the object, on a plane of incidence of the object, and extracting a linearly polarized light component of the first polarization direction included in the light diffusely reflected by the object, a second light detector receiving the linearly polarized light component of the first polarization direction extracted by the separation optical element and a third light detector receiving the light diffusely reflected by the object.

Other objects, features and advantages of the present invention will become more apparent from the following detailed description when read in conjunction with the accompanying drawings.

DETAILED DESCRIPTION OF THE EMBODIMENTS

Figure 1:
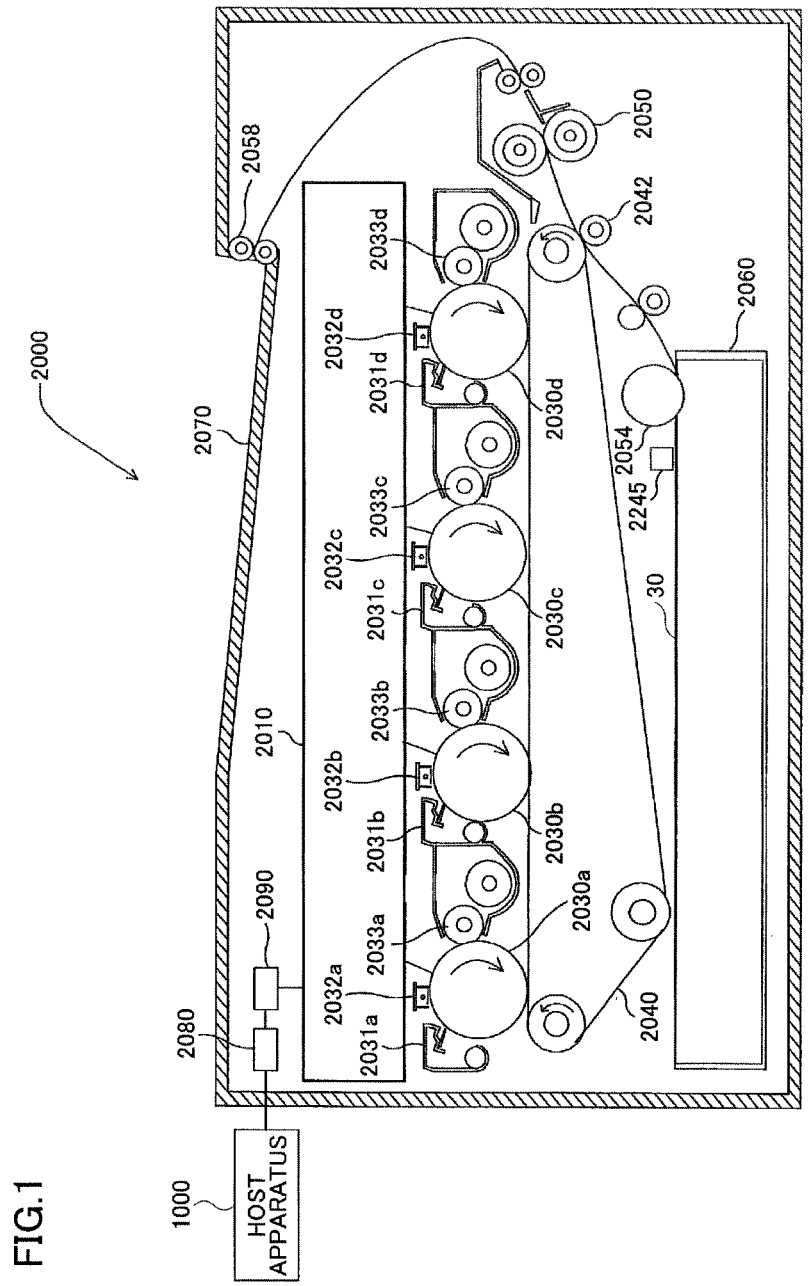
FIG. 1 illustrates a general configuration of a color laser printer according to one embodiment of the present invention.

Below, one embodiment of the present invention will be described using FIGS. 1 to 12. FIG. 1 shows a general configuration of a color printer 2000 according to the embodiment.

The color printer 2000 is a tandem-type multi-color color printer forming a full-color image by overlaying four colors (black, cyan, magenta and yellow), and includes an optical scanning device 2010; four photosensitive member drums (2030a, 2030b, 2030c and 2030d); four cleaning units (2031a, 2031b, 2031c and 2031d); four electrification devices (2032a, 2032b, 2032c and 2032d); four developing rollers (2033a, 2033b, 2033c and 2033d); a transfer belt 2040; a transfer roller 2042; a fixing device 2050; a paper supply roller 2054; a paper ejection roller 2058; a paper supply tray 2060; a paper ejection tray 2070; a communication control device 2080; an optical sensor 2245; and a printer control device 2090 that controls the above-mentioned respective parts in an overall manner.

The communication control device 2080 controls bidirectional communication with a host apparatus (for example, a personal computer) 1000 via a network or the like.

The printer control device 2090 includes a CPU, a ROM storing programs described by codes decodable by the CPU and various data used upon executing the programs; a RAM as a work memory; an amplifier circuit; and an AD converter circuit converting analog data into digital data. The printer control device 2090 controls the respective parts of the color printer 2000 in response to a request from the host apparatus 1000, and also, transmits image information from the host apparatus 1000 to the optical scanning device 2010.

The photosensitive member drum 2030a, the electrification device 2032a, the developing roller 2033a and the cleaning unit 2031a are used as a set, and form an image forming station for forming a black image (hereinafter, referred to as a "K station" for the sake of convenience).

The photosensitive member drum 2030b, the electrification device 2032b, the developing roller 2033b and the cleaning unit 2031b are used as a set, and form an image forming station for forming a cyan image (hereinafter, referred to as a "C station" for the sake of convenience).

The photosensitive member drum 2030c, the electrification device 2032c, the developing roller 2033c and the cleaning unit 2031c are used as a set, and form an image forming station for forming a magenta image (hereinafter, referred to as a "M station" for the sake of convenience).

The photosensitive member drum 2030d, the electrification device 2032d, the developing roller 2033d and the cleaning unit 2031d are used as a set, and form an image forming station for forming a yellow image (hereinafter, referred to as a "Y station" for the sake of convenience).

A photosensitive layer is formed on the surface of each one of the respective photosensitive member drums 2030a to 2030d. That is, the surfaces of the respective photosensitive member drums are to-be-scanned surfaces. It is noted that the respective photosensitive member drums are rotated in the directions of arrows in FIG. 1 by a rotation mechanism not shown.

The respective electrification devices 2032a to 2032d uniformly electrify the surfaces of the photosensitive member drums 2030a to 2030d, respectively.

The optical scanning device 2010 scans the electrified surfaces of the corresponding photosensitive member drums 2030a to 2030d, respectively, with light modulated for the respective colors based on multi-color image information (black image information, cyan image information, magenta image information and yellow image information) from the printer control device 2090. Thus, latent images corresponding to the image information are formed on the surfaces of the respective photosensitive member drums 2030a to 2030d, respectively. The thus formed latent images move toward the corresponding developing rollers 2033a to 2033d as the photosensitive member drums 2030a to 2030d rotate, respectively.

Toners from corresponding toner cartridges (not shown) are thinly coated uniformly on the surfaces of the respective developing rollers 2033a to 2033d as they rotate. Then, when the toners on the surfaces of the respective developing rollers 2033a to 2033d come into contact with the surfaces of the photosensitive member drums 2030a to 2030d, they move to only parts on the surfaces irradiated by light, and adhere thereto. That is, the respective developing rollers 2033a to 2033d cause the toners to adhere to the latent images formed on the surfaces of the respective photosensitive member drums 2030a to 2030d, and thus visualize them. Then, the images formed upon the adherence of the toners thereto (toner images) move toward the transfer belt 2040 as the photosensitive member drums 2030a to 2030d rotate.

The respective toner images of yellow, magenta, cyan and black are transferred onto the transfer belt 2040 in sequence in predetermined timing, and a multi-color image is formed when they are thus overlaid together.

Recording paper 30 is stored in the paper supply tray 2060. Near the paper supply tray 2060, the paper supply roller 2054 is placed. The paper supply roller 2054 takes out the recording paper 30 from the paper supply tray, sheet by sheet. The sheet of recording paper 30 is sent out toward the space between the transfer belt 2040 and the transfer roller 2042 in predetermined timing. Thus, the toner image on the transfer belt 2040 is transferred to the sheet of recording paper 30. The sheet of recording paper 30 onto which the toner image is thus transferred is sent to the fixing device 2050.

In the fixing device 2050, heat and pressure are applied to the sheet of recording paper 30. Thus, the toner image is fixed onto the sheet of recording paper 30. The sheet of recording paper 30 onto which the toner image is thus fixed is sent to the paper ejection tray 2070 via the paper ejection roller 2058, and is stacked onto the paper ejection tray 2070, sheet by sheet.

The respective cleaning units 2031a to 2031d remove toners (residual toners) left on the surfaces of the corresponding photosensitive member drums 2030a to 2030d, respectively. The surfaces of the photosensitive member drums 2030a to 2030d from which the residual toners are thus removed are returned to the positions facing the corresponding electrification devices 2032a to 2032d again, respectively.

The optical sensor 2245 is used to identify the brand of the recording paper 30 contained in the paper supply tray 2060.

Figure 2:
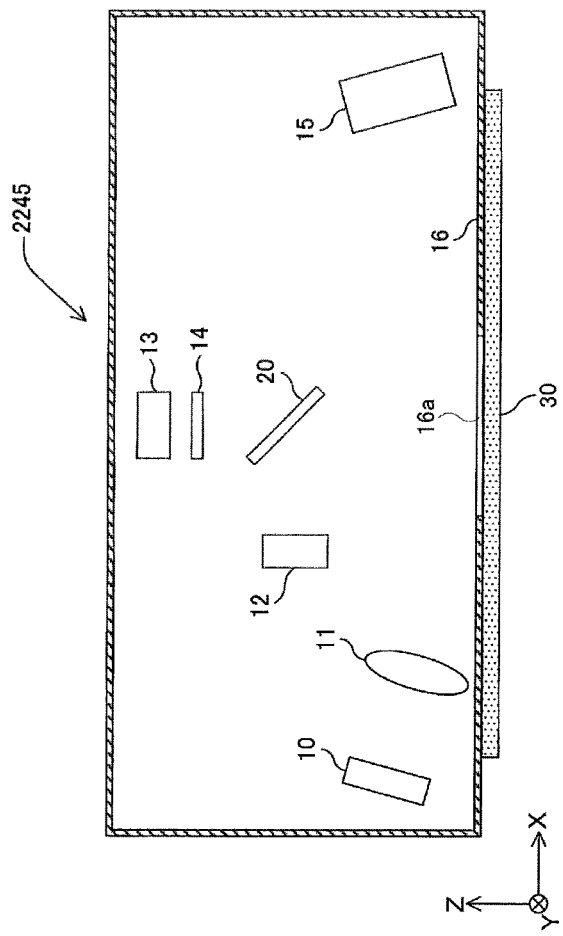
FIG. 2 illustrates a configuration of an optical sensor in FIG. 1.

For example, as shown in FIG. 2, the optical sensor 2245 has a light source 10, a collimator lens 11, a polarization filter 14, three optical receivers (12, 13 and 15), a half mirror 20 and a dark box 16 containing them.

The dark box 16 is a box member made of metal, and for example, is a box member made of aluminium. In order to reduce the influence of disturbance light and stray light, a black alumite treatment is carried out on the surface thereof.

It is noted that description will be made assuming that in a XYZ three-dimensional coordinate system, the Z-axis direction corresponds to the direction perpendicular to the surface of a sheet of recording paper 30, and the X-Y plane corresponds to a plane parallel to the surface of the sheet of recording paper 30. The optical sensor 2245 is placed on the +Z side of the sheet of recording paper 30.

Figure 3:
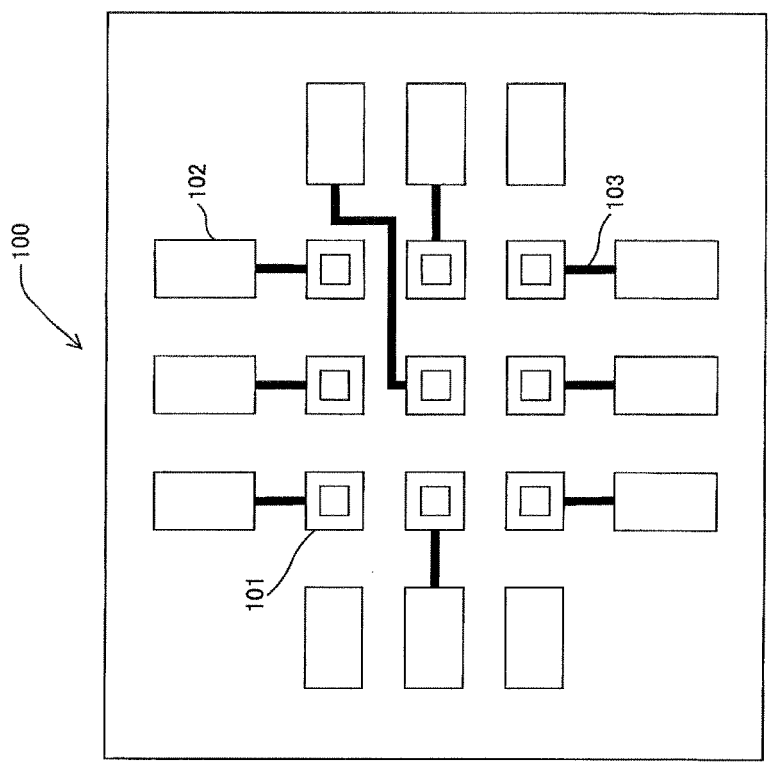
FIG. 3 illustrates a vertical cavity surface emitting laser array.
Figure 4:
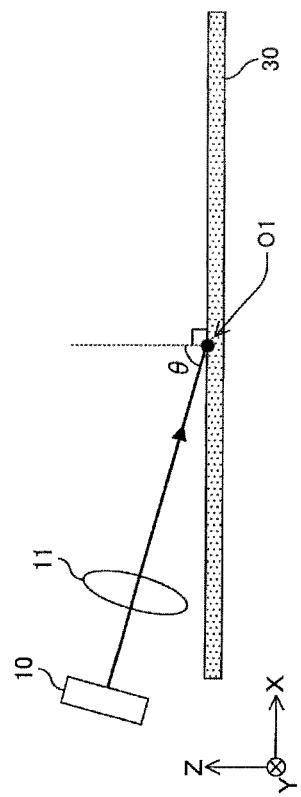
FIG. 4 illustrates an incident angle of incident light on recording paper.

The light source 10 has plural light-emitting parts 101 (see FIG. 3) formed on a common substrate. The light-emitting parts 101 are connected with respective electrode pads 102 via wiring materials 103, respectively. The respective light-emitting parts 101 are vertical cavity surface emitting lasers (VCSEL). That is, the light source includes a vertical cavity surface emitting laser array (VCSEL array) 100. For example, as shown in FIG. 3, the nine light-emitting parts 101 are arranged two-dimensionally.

The light source 10 is placed in such a manner that linearly polarized light of S-polarized light is emitted therefrom to the sheet of recording paper 30. Further, the incident angle $\theta$ of the light onto the sheet of recording paper 30 from the light source 10 is 80° (see FIG. 4).

The collimator lens 11 is placed on the light path of the light emitted by the light source 10, and makes the light be approximately parallel light. The light that has passed through the collimator lens 11 then irradiates the sheet of recording paper 30 via an opening 16a formed on the dark box 16. Hereinafter, the center of the irradiated area on the surface of the sheet of recording paper 30 will be referred to as an "irradiation center" ("O1" in the case of FIGS. 4 and 5). Further, the light that has passed through the collimator lens 11 will also be referred to as "irradiation light".

It is noted that when light is incident on a boundary surface of a medium, the plane including the incident light beam and the normal to the boundary surface passing through the incident point is called a "plane of incidence". In a case where incident light includes plural light beams, planes of incidence exist for the respective light beams. However, for the sake of convenience, only the plane of incidence of the light beam incident at the irradiation center will be referred to as a "plane of incidence of a sheet of recording paper". That is, the plane including the irradiation center and parallel to the X-Z plane is the plane of incidence of the sheet of recording paper 30.

The half mirror 20 is placed on the +Z side of the irradiation center O1. The half mirror 20 has a beam dividing plane that divides incident light into transmitted light and reflected light. The beam dividing plane is set in such a manner that the ratio between the amount of transmitted light and the amount of reflected light can be approximately 1:1. Hereinafter, the reflectance of the half mirror 20 will be referred to as "Rr" and the transmittance of the half mirror 20 will be referred to as "Rt". It is also possible to use a beam splitter having an equal function instead of the half mirror 20.

The optical receiver 12 is placed on the light path of the light reflected by the half mirror 20.

The polarization filter 14 is placed on the light path of the light that has passed through the half mirror 20. The polarization filter 14 transmits S-polarized light and blocks P-polarized light.

Figure 5:
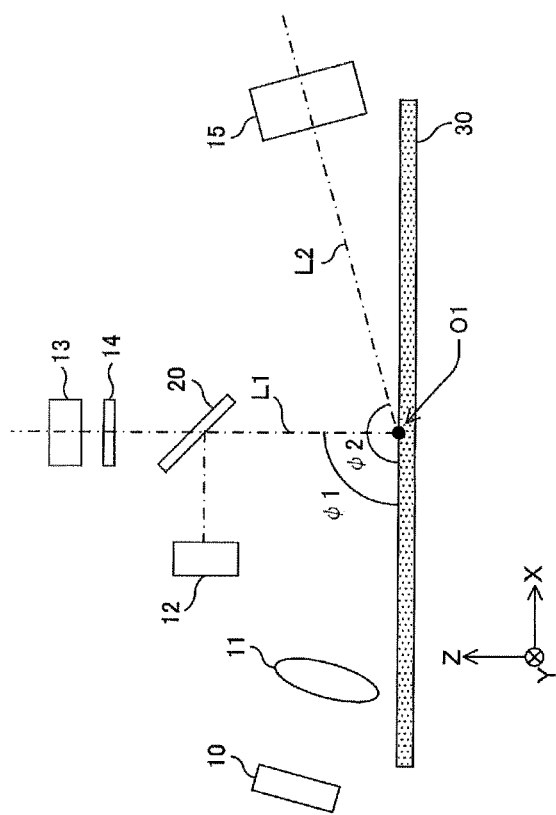
FIG. 5 illustrates positions of two optical receivers.
Figure 6A:
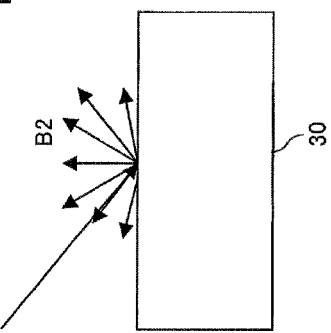
FIG. 6A illustrates surface specularly-reflected light.
Figure 6B:
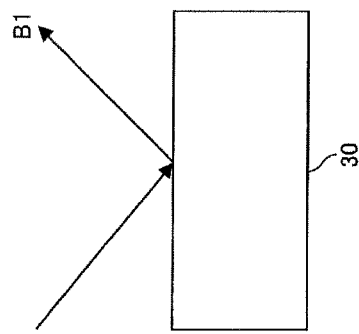
FIG. 6B illustrates surface diffusely-reflected light.
Figure 6C:
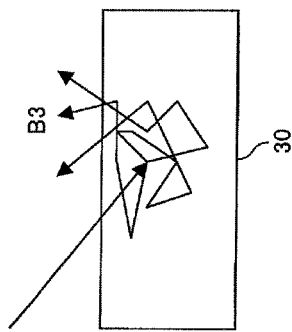
FIG. 6C illustrates inside diffusely-reflected light.

The optical receiver 13 is placed on the +Z side of the polarization filter 14. That is, the optical receiver 13 receives light that has passed through the polarization filter 14. As shown in FIG. 5, the angle $\theta 1$ of the line L1 connecting the irradiation center O1 and the respective centers of the half mirror 20, the polarization filter 14 and the optical receiver 13 from the surface of the sheet of recording paper 30 is 90°. That is, the line L1 is coincident with a normal to the surface of the sheet of recording paper 30 at the irradiation center O1.

The optical receiver 15 is placed on the +X side of the irradiation center O1 concerning the X-axis direction. Then, the angle $\phi 2$ of the line L2 connecting the irradiation center O1 and the center of the optical receiver 15 from the surface of the recording paper 30 is 170° (see FIG. 5).

The center of the light source 10, the irradiation center O1, the center of polarization filter 14, the center of the optical receiver 12, the center of the optical receiver 13 and the center of the optical receiver 15 exist on approximately the same plane.

The reflected light from the sheet of recording paper 30 when the sheet of recording paper is irradiated with light can be regarded as reflected light reflected by the surface of the sheet of recording paper 30 and reflected light reflected by the inside of the sheet of recording paper 30, separately. Further, the reflected light reflected by the surface of the sheet of recording paper 30 can be regarded as reflected light having been specularly reflected and reflected light having been diffusely reflected, separately. Hereinafter, for the sake of convenience, the reflected light specularly reflected by the surface of the sheet of recording paper 30 will also be referred to as "surface specularly-reflected light" ("B1" in a case of FIG. 6A). The reflected light diffusely reflected by the surface of the sheet of recording paper 30 will also be referred to as "surface diffusely-reflected light" ("B2" in a case of FIG. 6B).

The surface of the sheet of recording paper 30 includes flat surface parts and inclined surface parts. The smoothness of the surface of the sheet of recording paper 30 depends on the ratio between the flat surface parts and the inclined surface parts. Light reflected by the flat surface parts is surface specularly-reflected light. Light reflected by the inclined surface parts is surface diffusely-reflected light. Surface diffusely-reflected light is reflected light reflected completely in a scatter reflection manner, and the reflection directions thereof can be regarded as having isotropy. As the smoothness of the surface of the sheet of recording paper 30 increases, the amount of surface specularly-reflected light increases.

On the other hand, in a case where recording paper 30 is ordinary printing paper, reflected light from the inside of the sheet of the recording paper 30 includes only diffusely-reflected light since multiple scattering occurs in the fibers inside. Hereinafter, for the sake of convenience, the reflected light from the inside of the sheet of recording paper 30 will be referred to as "inside diffusely-reflected light" ("B3" in a case of FIG. 6C). The same as or similar to the surface diffusely-reflected light, the inside diffusely-reflected light is reflected light having been reflected completely in a scatter reflection manner, and the reflection directions thereof can be regarded as having isotropy.

The polarization directions of the surface specularly-reflected light and the surface diffusely-reflected light are the same as the polarization directions of the irradiation light. In order that the polarization direction is to be rotated on the surface of a sheet of recording paper 30, the irradiation light should be reflected by a surface that is inclined to the direction of the rotation with respect to the optical axis. Here, the center of the light source 10, the irradiation center O1 and the centers of the respective optical receivers exist on the same plane. Thus, the reflected light of which the polarization direction is rotated on the surface of the sheet of recording paper 30 is not reflected to the direction of any one of the optical receivers.

On the other hand, the polarization direction of the inside diffusely-reflected light is rotated with respect to the polarization direction of the irradiation light. This is because it is regarded that the light entering the inside of the sheet of recording paper 30 is optically rotated upon passing through the fibers and undergoing multiple scattering, and thus, the polarization direction is rotated.

Figure 7:
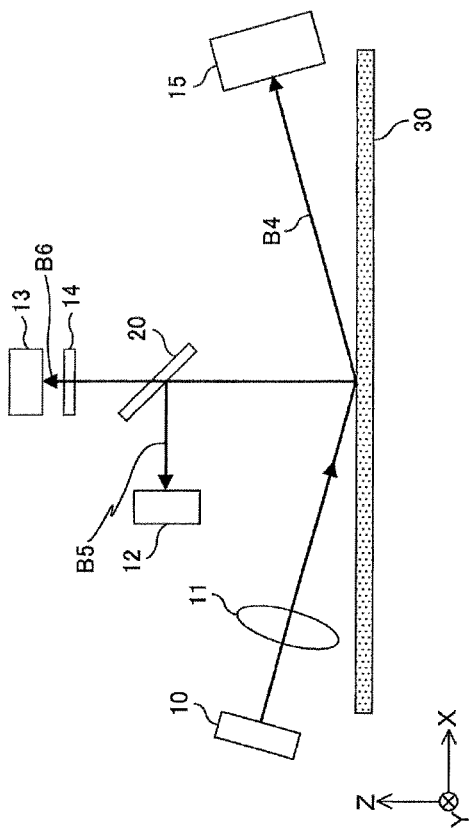
FIG. 7 illustrates light received by each optical receiver.

Thus, the optical receiver 12 receives the surface diffusely-reflected light and the inside diffusely-reflected light (see FIG. 7). In FIG. 7, B5 denotes "surface diffusely-reflected light+inside diffusely-reflected light". Also on the polarization filter 14, the surface diffusely-reflected light and inside diffusely-reflected light are incident. The polarization direction of the surface diffusely-reflected light is of S-polarized light the same as the polarization direction of the irradiation light. Thus, the surface diffusely-reflected light passes through the polarization filter 14.

On the other hand, the polarization direction of the inside diffusely-reflected light is rotated with respect to the polarization direction of the irradiation light. Thus, the P-polarized light component included in the inside diffusely-reflected light is blocked by the polarization filter 14. That is, the surface diffusely-reflected light and only the S-polarized light component included in the inside diffusely-reflected light are received by the optical receiver 13 (see FIG. 7). In FIG. 7, "B6" denotes "surface diffusely-reflected light+S-polarized light component of inside diffusely-reflected light". Thus, the difference between the amount of received light of the optical receiver 12 and the amount of received light of the optical receiver 13 is the amount of light of the P-polarized light component included in the inside diffusely-reflected light.

It is noted that hereinafter, the P-polarized light component included in the inside diffusely-reflected light will also be referred to as "the P-polarized light component of the inside diffusely-reflected light". Similarly, the S-polarized light component included in the inside diffusely-reflected light will also be referred to as "the S-polarized light component of the inside diffusely-reflected light".

The inventors and so forth confirmed that the amount of light of the inside diffusely-reflected light has correlation with the thickness and/or the density of the sheet of recording paper 30. This is because the amount of light of the inside diffusely-reflected light depends on the path length when the light passes through the fibers of the sheet of recording paper 30.

On the optical receiver 15, the surface specularly-reflected light and small amounts of the surface diffusely-reflected light and the inside diffusely-reflected light are incident. That is, on the optical receiver 15, chiefly the surface specularly-reflected light is incident (see FIG. 7). "B4" in FIG. 7 denotes "surface specularly-reflected light".

The optical receivers 12, 13 and 15 output electric signals corresponding to the amounts of received light (photoelectric converted signals) to the printer control device 2090, respectively. It is noted that hereinafter, "S1$a$" denotes the signal level of the output signal of the optical receiver 12 when the light source 10 emits the light to the sheet of recording paper 30; "S1$b$" denotes the signal level of the output signal of the optical receiver 13 when the light source 10 emits the light to the sheet of recording paper 30; and "S2" denotes the signal level of the output signal of the optical receiver 15 when the light source 10 emits the light to the sheet of recording paper 30.

The printer control device 2090 calculates a signal level "S1" based on the following formula (1):

$$S1=(S1a/Rr)-(S1b/Rt) \quad (1)$$

"S1" calculated from the above-mentioned formula (1) corresponds to the amount of light of the P-polarized light component included in the inside diffusely-reflected light. It is noted that the specific calculation method is not necessarily limited thereto.

Here, concerning plural brands of recording paper 30 that the color printer 2000 can use, the values of S1 and S2 are previously measured for the respective brands of recording paper 30 during a pre-shipment process such as an adjustment process, and the measurement results are stored in the ROM of the printer control device 2090 in a form of a "recording paper identification table".

Figure 8:
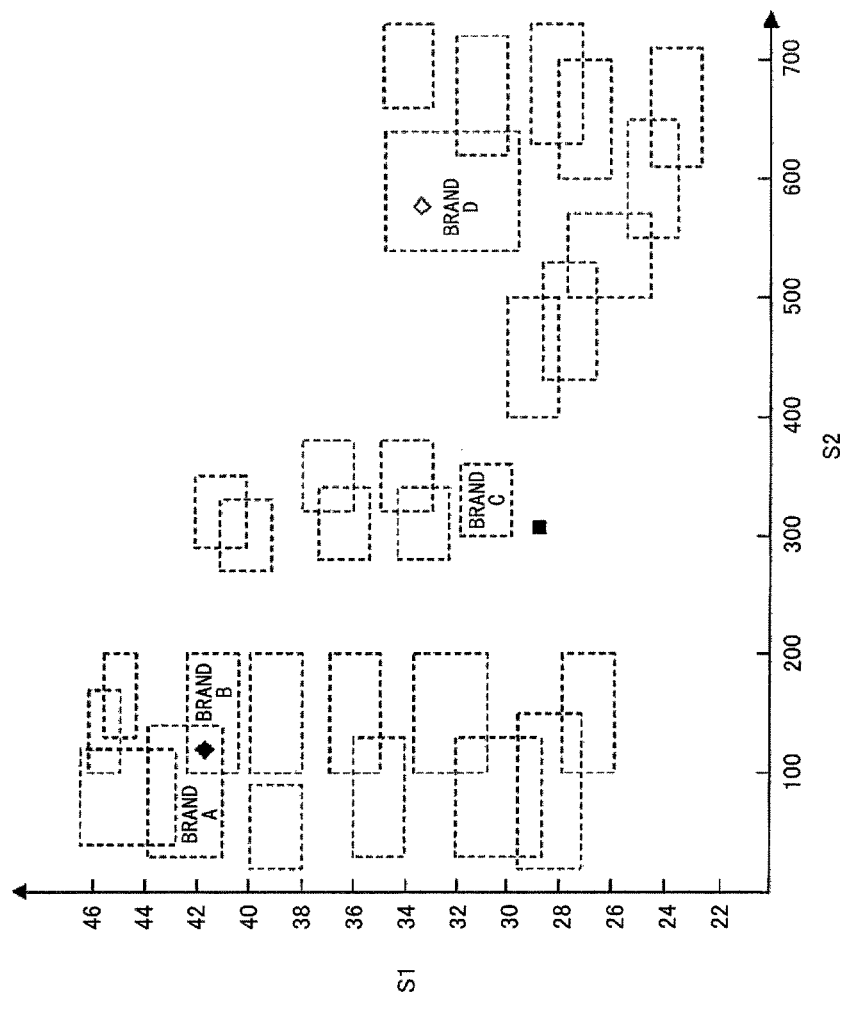
FIG. 8 illustrates a relationship of S1 and S2 with a brand of recording paper.

FIG. 8 shows the measurement results of S1 and S2 concerning 30 brands of recording paper 30 on the domestic market. Each frame (defined by a broken line) represents a range of dispersion of the same brand. For example, when "◇" in FIG. 8 represents the measured values of S1 and S2 of recording paper 30, the brand of this recording paper 30 is identified as a brand D. When "■" in FIG. 8 represents the measured values of S1 and S2 of recording paper 30, the brand of this recording paper 30 is identified as a brand C that is nearest. When "◆" in FIG. 8 represents the measured values of S1 and S2 of recording paper 30, the brand of this recording paper 30 is identified as any one of brands A and B.

At this time, the differences between the average values of the brand A and the measured values, and the differences between the average values of the brand B and the measured values are calculated. Then, the brand for which the differences are smaller is determined to correspond to the measured values. Further, it is also possible to calculate the dispersion of the brand A assuming that the measured values belong to the brand A, calculate the dispersion of the brand B assuming that the measured values belong to the brand B, and the brand having the smaller dispersion may be determined to correspond to the measured values.

In the related art, recording paper is identified as a result of detecting the glossiness of the surface of the recording paper being detected from the amount of specularly-reflected light, and smoothness of the recording paper surface being detected from the ratio between the amount of specularly-reflected light and the amount of diffusely-reflected light. In contrast thereto, according to the embodiment, not only the glossiness and the smoothness of the surface of the recording paper 30, but also information including the thickness and the density that are other characteristics of the recording paper 30 are detected from reflected light, and thus, the number of types of recording paper 30 that can be identified is increased in comparison to the related art.

For example, only by the information of the surface of recording paper used in the identification method of the related art, it may be difficult to distinguish between plain paper and matt coated paper. However, according to the embodiment, by adding information concerning the inside of recording paper to information concerning the surface of recording paper, it is possible to distinguish not only between plain paper and matt coated paper, but also between plural brands of plain paper and plural brands of matt coated paper, respectively.

That is, according to the embodiment, it is possible to identify the brand of the object from among plural types of recording paper among which at least any one of the glossiness, smoothness, thickness and density is different.

Further, for plural brands of recording paper 30 that the color printer 2000 can use, most suitable development conditions and transfer conditions are determined for each station for each one of the respective brands of recording paper 30 during a pre-shipment process such as an adjustment process, and the determination results are stored in the ROM of the printer control device 2090 in a form of a "development and transfer table".

At a time of starting of the power supply in the color printer 2000, at a time of recording paper 30 being supplied to the paper supply tray 2060, and so forth, the printer control device 2090 carries out a paper type identification process on the recording paper 30. This paper type identification process that the printer control device 2090 carries out will be described now.

(1) The plural light-emitting parts 101 (of the light source 10) of the optical sensor 2245 are caused to emit light simultaneously.

(2) The values of S1 and S2 are obtained from the output signals of the optical receivers 12, 13 and 15.

(3) Using the above-mentioned "recording paper identification table", the brand of the recording paper 30 is identified from the thus obtained values of S1 and S2.

(4) The thus identified brand of the recording paper 30 is stored in the RAM, and the paper type identification process is finished.

Upon receiving a print job request, the printer control device 2090 reads the brand of the recording paper 30 thus stored in the RAM, and obtains the development conditions and transfer conditions most suitable for the brand of the recording paper 30 from the above-mentioned "development and transfer table".

Then, the printer control device 2090 controls the developing devices and the transfer devices of the respective stations according to the thus obtained most suitable development conditions and transfer conditions. For example, the printer control device 2090 controls the transfer voltage to be applied to the transfer roller 2042 and/or the toner amounts to be supplied to the photosensitive member drums 2030a to 2030d, respectively. Thereby, the color printer 2000 can form an image of high quality on the sheet of recording paper 30.

The diffusely-reflected light from the sheet of recording paper 30 includes A: "the surface diffusely-reflected light", B: "the S-polarized light component of the inside diffusely-reflected light", and C: "the P-polarized light component of the inside diffusely-reflected light".

In an apparatus using a sensor in the related art, the amount of light of the diffusely-reflected light (A+B+C) is detected, and a type of recording paper is identified from among two or three types of recording paper. On the other hand, according to the embodiment, the amount of the S-polarized light component of the inside diffusely-reflected light is detected, and the type of recording paper 30 is identified from among at least ten types of recording paper 30. Thus, it is possible to carry out paper identification five times or more as detailed as the related art.

When the irradiation light is S-polarized light, the ratio of the amount of light of the S-polarized light component of the inside diffusely-reflected light to the diffusely-reflected light (A+B+C) is on the order of 40% at most. Further, a polarization filter of low cost such as that mounted in an ordinary sensor has low transmission, and by the polarization filter, the amount of light is attenuated to about 80%. Therefore, the S-polarized light component of inside diffusely-reflected light is attenuated by the polarization filter 14 upon being separated thereby, and thus, the amount of light becomes substantially about 30%.

The amount of the S-polarized light amount of the inside diffusely-reflected light is thus attenuated to substantially about 30% of the amount of the diffusely-reflected light (A+B+C). Therefore, as the amount of the irradiation light, 3.3 times as much as the amount of light of the related art is required. Further, in order to carry out paper identification five times or more as detailed as the related art, it is necessary to irradiate the amount of light 3.3×5 times as much as the related art.

In a case of using a non-polarizing light source such as a LED, it is necessary to obtain linearly polarized light (S-polarized light) by causing light to pass through a polarization filter before irradiating the sheet of recording paper 30, in order to irradiate S-polarized light to the sheet of recording paper 30. At this time, when the polarization filter of low cost is used as the above-mentioned case, the amount of light to be irradiated to the sheet of recording paper 30 becomes approximately 40% (=50% (corresponding to the amount of the P-polarized light being cut off)×80% (attenuation in the polarization filter)) of the amount of light emitted by the LED.

Therefore, in the case of using the LED, it is necessary to emit the amount of light 40 times or more (=3.3×5/0.4) as much as the related art. However, the amount of irradiation light of a LED of low cost in the related art is on the order of several milliwatts (typically, 1 mW), and it may be difficult to obtain 40 times thereof (at least 40 mW) of the amount of irradiation light from the LED.

On the other hand, from a vertical cavity surface emitting laser array, it is possible to easily obtain a desired amount of irradiation light by simultaneously causing plural light-emitting parts to emit light.

Further, in order to detect the S-polarized light component of the inside diffusely-reflected light with high accuracy, it is preferable to further satisfy the following two light receiving conditions:

(1) The detection of the S-polarized light component of the inside diffusely-reflected light is not carried out at least in a direction in which the surface specularly-reflected light is included.

This is because, it is difficult for the irradiation light to include only S-polarized light perfectly, and thus, the reflected light on the surface inevitably includes a P-polarized light component. Therefore, in a direction in which the surface specularly-reflected light is included, the P-polarized light component incident on the polarization filter 14 is increased. Further, it is difficult to carry out complete polarization separation by the polarization filter 14, and thus, a part of the P-polarized light component is inevitably transmitted thereby according to its extinction ratio. If the polarization filter 14 and the optical receiver 13 were placed in a direction including the surface specularly-reflected light, the optical receiver 13 would detect the amount of light including the P-polarized light component, and it could not be possible to detect with high accuracy the S-polarized light component of the inside diffusely-reflected light necessary to detect information of the inside of the recording paper 30.

It is noted that it is possible to consider using a polarization filter having a high extinction ratio so as to perfectly separate one polarized light component from incident light. However, such a way may result in cost increase.

(2) The detection of the inside diffusely-reflected light is carried out in the direction of the normal to the sheet of recording paper 30 at the irradiation center.

This is because, inside diffused-reflected light can be regarded as having complete diffuse reflection, and thus, the amount of reflected light in the detection direction can be approximated by Lambertian distribution, and the amount of reflected light is maximized in the normal direction at the irradiation center. By placing the polarization filter 14 and the optical receivers 12 and 13 on the light path of light reflected in the normal direction at the irradiation center, the S/N ratio is high, and the accuracy is maximized. Further, as a result of the optical receivers 12 and 13 receiving the light divided by the half mirror 20, the respective optical receivers 12 and 13 can detect the light of the same diffuse reflection direction. Therefore, it is possible to ignore a change in the amount of received light depending on the reflection direction from the irradiation center, i.e., a change in the amount of received light depending on the position of the optical receiver.

Next, a method of avoiding a speckle pattern will be described.

In a sensor detecting a surface state of a sheet of printing paper using the amount of reflected light, it is preferable to use a semiconductor laser in order to improve the S/N ratio. However, in this case, a speckle pattern may be generated as a result of coherent light emitted by the semiconductor laser being diffusely reflected by respective points of a rough surface such as a surface of a sheet of a recording paper, and interfering with one another.

A speckle pattern differs depending on an irradiated position, and thus, may cause a variation in the amount of received light of an optical receiver, and may cause degradation of identification performance. Thus, in the related art, a LED or the like is generally used as a light source.

The inventors and so forth used as a light source a vertical cavity surface emitting laser array (VCSEL array) in which plural light-emitting parts are two-dimensionally arranged (see FIG. 9), and obtained a relationship between the number of the light-emitting parts and a contrast ratio of a speckle pattern. Here, a value obtained from standardizing differences between the maximum values and the minimum values in observed intensity of a speckle pattern is defined as a contrast ratio of the speckle pattern. It is noted that hereinafter, for the sake of convenience, a contrast ratio of a specked pattern will be simply referred to as a "contrast ratio".

Observation of a speckle pattern was carried out using a beam profiler for a Y-axis direction (diffusion direction), and contrast ratios were calculated from the results of observation using the beam profiler. As samples, three types of plain paper (plain paper A, plain paper B and plain paper C) among which the smoothness is different, and gloss paper were used. The plain paper A is plain paper having Oken type smoothness of 33 seconds. The plain paper B is plain paper having Oken type smoothness of 50 seconds. The plain paper C is plain paper having Oken type smoothness of 100 seconds.

Figure 9:
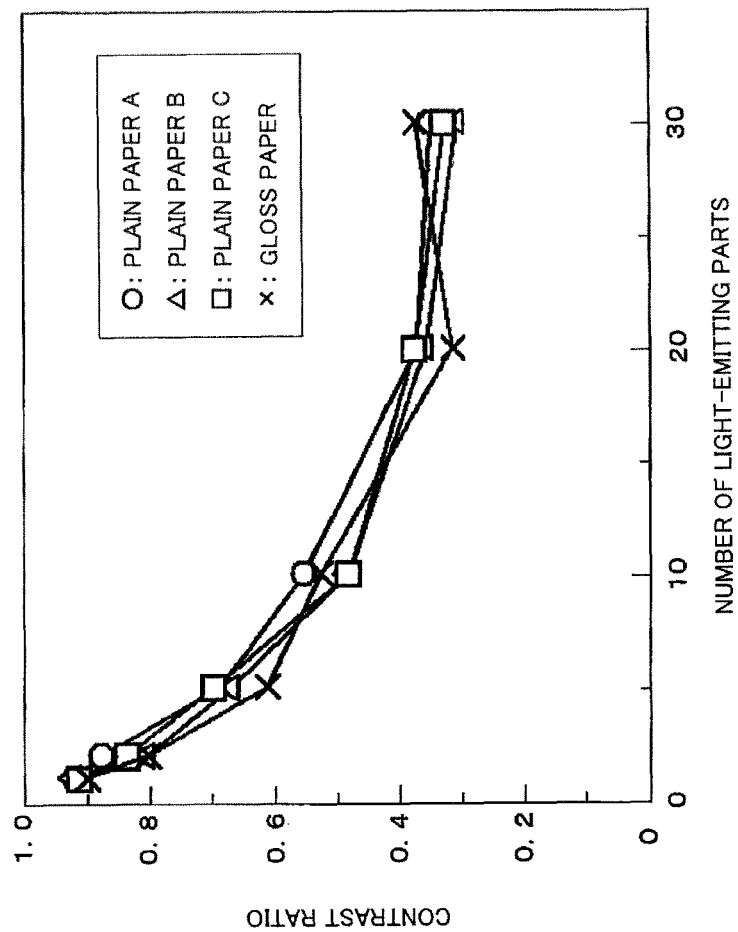
FIG. 9 illustrates influence of the number of light-emitting parts on the contrast ratio of a speckle pattern.

From FIG. 9, such a tendency is seen that, as the number of the light-emitting parts is increased, the contrast ratio is reduced. Further, it is seen that this tendency does not depend on the paper type.

Further, the inventors and so forth carried out an experiment for confirming that the effect of reduction of the contrast ratio is obtained not from the increase in the total amount of light but from the increase in the number of the light-emitting parts.

Figure 10:
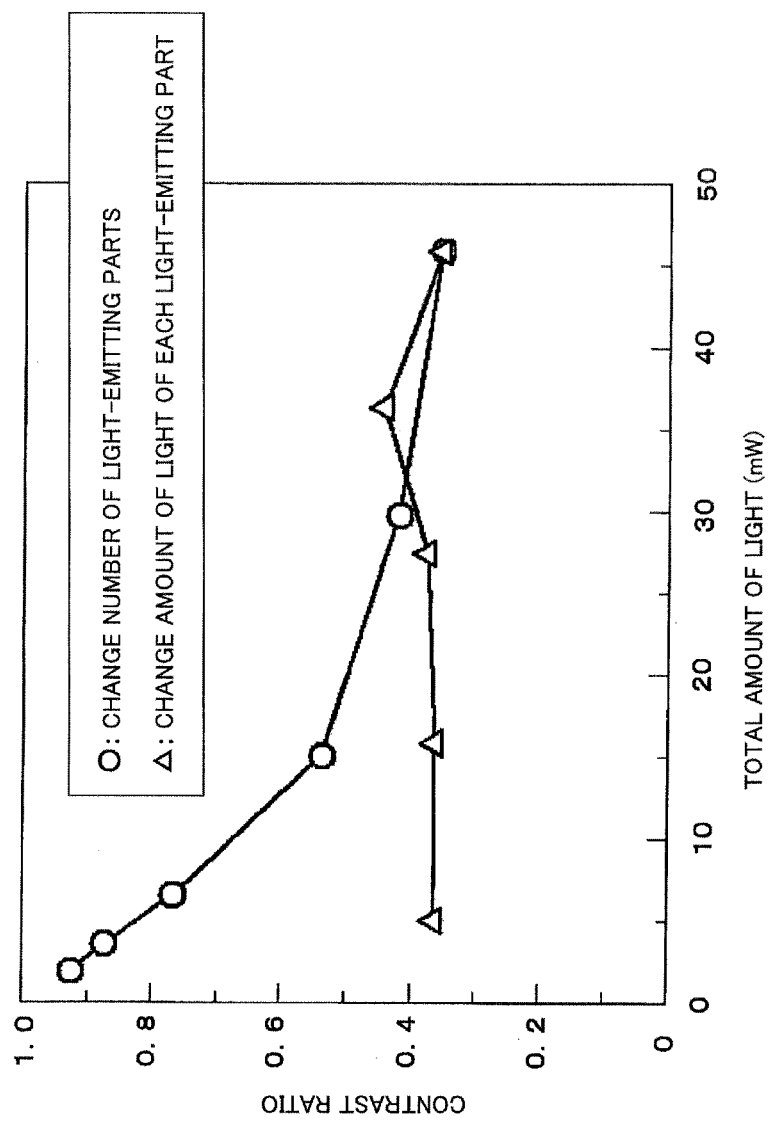
FIG. 10 illustrates a relationship between the contrast ratio of a speckle pattern and the total amount of light when the number of light-emitting parts is changed and when the amount of light of each light-emitting part is changed.
Figure 11:
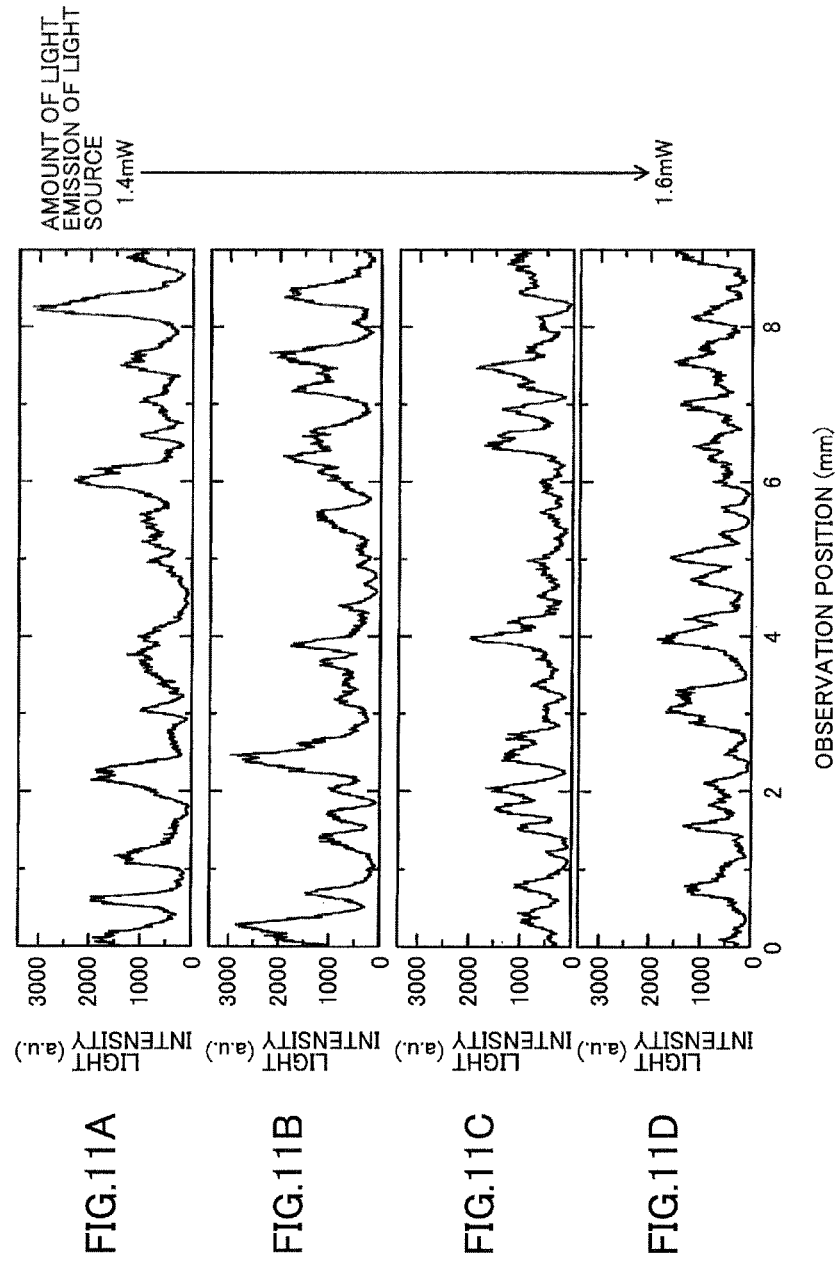
FIGS. 11A, 11B, 11C and 11D illustrate light intensity distributions of a speckle pattern when a driving current of a light source is changed.

FIG. 10 shows a relationship between the total amount of light and the contrast ratio for each one of a case where the amount of light of each light-emitting part was fixed (1.66 mW) and the number of the light-emitting parts was changed, and a case where the number of the light-emitting parts was fixed as 30 and the amount of light of each light-emitting part was changed.

In the case of changing the amount of light of each light-emitting part while keeping the number of the light-emitting parts unchanged (Δ), the contrast ratio is constant without regard to the amount of light. In contrast thereto, in the case of changing the number of the light-emitting parts while keeping the amount of light of each light-emitting part unchanged (○), the contrast ratio is large when the number of light-emitting parts is small, and the contrast ratio falls as the number of light-emitting parts increases. Therefrom, it is confirmed that the effect of reduction of the contrast ratio is obtained not from the increase in the amount of light but from the increase in the number of the light-emitting parts.

Further, the inventors and so forth studied as to whether it is possible to avoid a speckle pattern by temporally changing the wavelength of light that is emitted by the light source.

In a vertical cavity surface emitting laser (VCSEL), it is possible to control the wavelength of emitted light by controlling the driving current. This is because upon a change in the driving current, the refractive index is changed from a temperature change of the inside of the vertical cavity surface emitting laser, and thus, the effective length of the resonator is changed.

FIGS. 11A, 11B, 11C and 11D show light intensity distributions obtained from observation of a speckle pattern using a beam profiler while the amount of emitted light is changed from 1.4 mW to 1.6 mW upon a change of the driving current of the light source 10. From FIGS. 11A to 11D, it is confirmed that as the driving current is changed, that is, the wavelength of the light emitted by the light source is changed, a light intensity distribution is changed.

Figure 12:
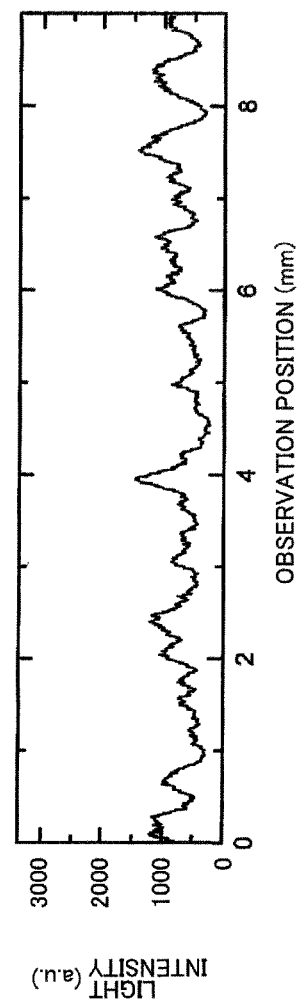
FIG. 12 illustrates an effective light intensity distribution when the driving current of the light source is changed at high speed.

FIG. 12 shows an effective light intensity distribution for a case where the driving current is changed at high speed. This light intensity distribution is equal to the average of the light intensity distributions at the plural driving currents, and the fluctuation of the light intensity is suppressed. The contrast ratio in the case where the driving current is changed at high speed is 0.72, and thus, is reduced from the contrast ratio 0.96 in a case where the driving current is fixed.

That is, it is seen that, by temporally changing the wavelength of the irradiation light, a speckle pattern is suppressed. Thus, it is possible to reduce the contrast ratio by making the driving current have the current value that is changed temporally in a manner of, for example, a triangular wave.

According to the embodiment, the light source 10 of the optical sensor 2245 includes the vertical cavity surface emitting laser array 100 in which the nine light-emitting parts 101 are arranged two-dimensionally, and the CPU (not shown) of the printer control device 2090 supplies the driving current having a form of a triangle wave to the vertical cavity surface emitting laser array 100. Thereby, a speckle pattern is suppressed, and precise detection of the amount of reflected light is made possible. Therefore, it is possible to improve the accuracy of identifying recording paper 30.

It is noted that according to the surface nature identification apparatus disclosed by Patent Reference No. 1 and the printing apparatus disclosed by Patent Reference No. 2, there may be a possibility that the surface of a recording material may be scratched, and the surface characteristics themselves may be changed.

According to the recording material identification apparatus disclosed by Patent Reference No. 3, only recording materials having different smoothness can be distinguished, and it is not possible to distinguish recording materials having the same smoothness and different thickness.

According to the sheet material identification apparatus disclosed by Patent Reference No. 4, the identification is carried out based on the amount of specularly-reflected light. That is, the inside of an object is not considered, and the material of a sheet material is determined only using the absolute amount of specularly-reflected light.

According to the image forming apparatus disclosed by Patent Reference No. 5, the amount of reflected light from an object is detected in plural directions. Also in this case, the inside of an object is not considered, glossiness is detected from the ratio between specularly-reflected light and diffusely-reflected light, and the paper type is determined.

According to the image forming apparatus disclosed by Patent Reference No. 6, specularly-reflected light is separated into two polarized light components and detected, the smoothness of the surface of paper is detected using the difference between the amounts of these light components, and the paper type is determined. In this case, polarized light is used. However, detection is made in a direction including specularly-reflected light, and, also in this case, the inside of an object is not considered.

That is, the sheet material identifying apparatus disclosed by Patent Reference No. 4 and the image forming apparatuses disclosed by Patent References Nos. 5 and 6 can identify (distinguish) only non-coated paper, coated paper and an OHP sheet, and cannot identify the brand of paper necessary for forming an image of high quality.

Thus, according to the related art cases, identification of non-coated paper, coated paper and OHP sheet is carried out, but identification on the level of brands is not possible.

Further, for example, it is possible to further subdivide the identification levels by additionally mounting various sensors such as a sensor for detecting the thickness of a recording material using transmitted light, ultrasonic waves or the like, a sensor detecting the resistance value of a recording material, a temperature sensor and/or the like, in addition to the reflective optical sensors. However, if so, the number of parts/components is increased, the cost may increase and the size may increase.

According to the method of identifying recording paper of the embodiment, the method of identifying recording paper using the amount of internally diffused light including information of the inside of a sheet of recording paper which has not been considered so far is added to the method of identifying recording paper in the related art. In this case, in addition to the glossiness (smoothness) of a surface of recording paper in the related art, it is possible to also obtain information of the thickness and/or the density of the sheet of recording paper. Thereby, it is possible to identify recording paper in more detail. That is, it is possible to subdivide the identification levels.

Thus, according to the optical sensor 2245 of the embodiment, an irradiation system includes the light source 10 and the collimator lens 11. A first light detection system includes the optical receiver 15. A second light detection system includes the half mirror 20, the polarization filter 14 and the two optical receivers 12 and 13.

Thus, the optical sensor 2245 of the embodiment includes the light source 10, the collimator lens 11, the three optical receivers 12, 13 and 15, the polarization filter 14, the half mirror 20 and the dark box 16.

The optical receiver 12 receives the surface diffusely-reflected light and the inside diffusely-reflected light. The optical receiver 13 receives the surface diffusely-reflected light and the S-polarized light component of the inside diffusely-reflected light. The optical receiver 15 chiefly receives the surface specularly-reflected light. Then, the amount of the P-polarized light component of the inside diffusely-reflected light is calculated from the difference between the amount of reflected light received by the optical receiver 12 and the amount of reflected light received by the optical receiver 13. In this case, it is possible to obtain, with high accuracy, the amount of the P-polarized light component of the inside diffusely-reflected light.

The light source 10 includes the vertical cavity surface emitting laser array 100 that includes the plural light-emitting parts (VCSEL) 101. In this case, polarization filters for changing irradiation light into linearly polarized light are not necessary. Further, adjustment for changing the irradiation light into parallel light is made easier. Thus, it is possible to miniaturize the optical sensor 2245 and reduce the cost of the optical sensor 2245.

Further, in the vertical cavity surface emitting laser array 100, it is possible to increase the density of the plural light-emitting parts 101 (integrate them into a high density pattern). Such an integration into a high density pattern is difficult with a LED or the like that is used in the related art. In this case, since it is possible to concentrate all the laser light beams near the optical axis of the collimator lens 11, it is possible to make the incident angles become uniform and make the plural light beams become approximately parallel light. Thus, it is possible to easily realize a collimating optical system.

The printer control device 2090 causes the plural light-emitting parts 101 of the vertical cavity surface emitting laser array 100 to simultaneously emit light. Thus, it is possible to increase the amount of the inside diffusely-reflected light, and also, it is possible to reduce the contrast ratio. Further, the printer control device 2090 temporally changes the wavelength of the light emitted by the light source 10. Thus, it is possible to suppress a speckle pattern.

That is, it is possible to separate reflected light from the inside of recording paper with high accuracy by the optical sensor 2245. In contrast thereto, it is difficult to separate reflected light from the inside of recording paper in the related art since the reflected light from the inside of recording paper is weak. The reflected light from the inside of recording paper includes information concerning the internal state of the recording paper.

The printer control device 2090 identifies the brand of recording paper from the output signal of the optical receiver 12, the output signal of the optical receiver 13 and the output signal of the optical receiver 15. That is, according to the embodiment, by taking the information concerning the internal state of recording paper into consideration, the level of identifying the paper type is improved into the level of the brand. In contrast thereto, it is difficult to identify the brand in the related art.

Further, the optical sensor 2245 according to the embodiment has such a component formation of not combining plural types of sensors and thus, has a simple component formation. Thus, it is possible to realize the optical sensor 2245 of a small size.

Thus, according to the optical sensor 2245, it is possible to identify the brand of recording paper 30 in more detail than the related art without much increasing the cost and size.

Since the color printer 2000 according to the embodiment includes the optical sensor 2245, it is possible to consequently form an image of high quality without much increasing the cost and size. Further, it is possible to remove the burden of manual setting which should be made in the related art, and eliminate a failure otherwise occurring from erroneous setting.

It is noted that for the above-mentioned embodiment, description has been made for a case where the light irradiated onto the recording paper 30 is S-polarized light. However, the light irradiated onto the recording paper 30 is not limited thereto. The light irradiated onto the recording paper may be P-polarized light, instead. However, in this case, a polarization filter that transmits P-polarized light is used instead of the polarization filter 14.

Further, in the above-mentioned embodiment, it is also possible to use, instead of the polarization filter 14, a polarization beam splitter or a wire-grid-type polarization filter having the equal function. However, in a case of using a reflective polarization filter such as a wire-grid-type polarization filter, this polarization filter reflects only S-polarized light, and the optical receiver 13 is placed on the light path of light reflected by the polarization filter.

Figure 13:
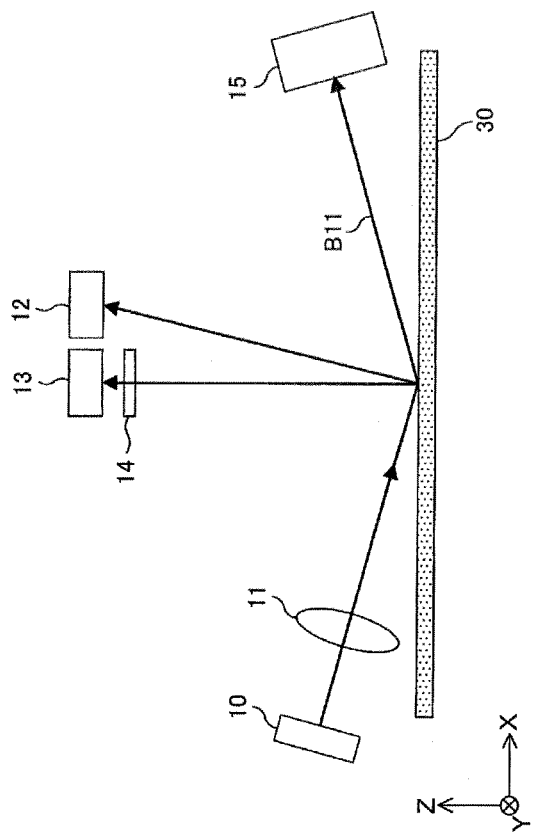
FIG. 13 illustrates a first variant of an optical sensor.

Further, in the above-mentioned embodiment, it is not necessary that the above-mentioned condition (2) is strictly satisfied. For example, as shown in FIG. 13, the optical receivers 12 and 13 may be placed adjacent to each other along the X-axis direction. It is noted that in FIG. 13, "B11" denotes surface specularly-reflected light. Further, it is also possible that the optical receivers 12 and 13 are placed adjacent to each other along the Y-axis direction. In any one of these cases, the half mirror 20 is not necessary, and it is possible to further miniaturize the optical sensor 2245 and reduce the cost.

Figure 14:
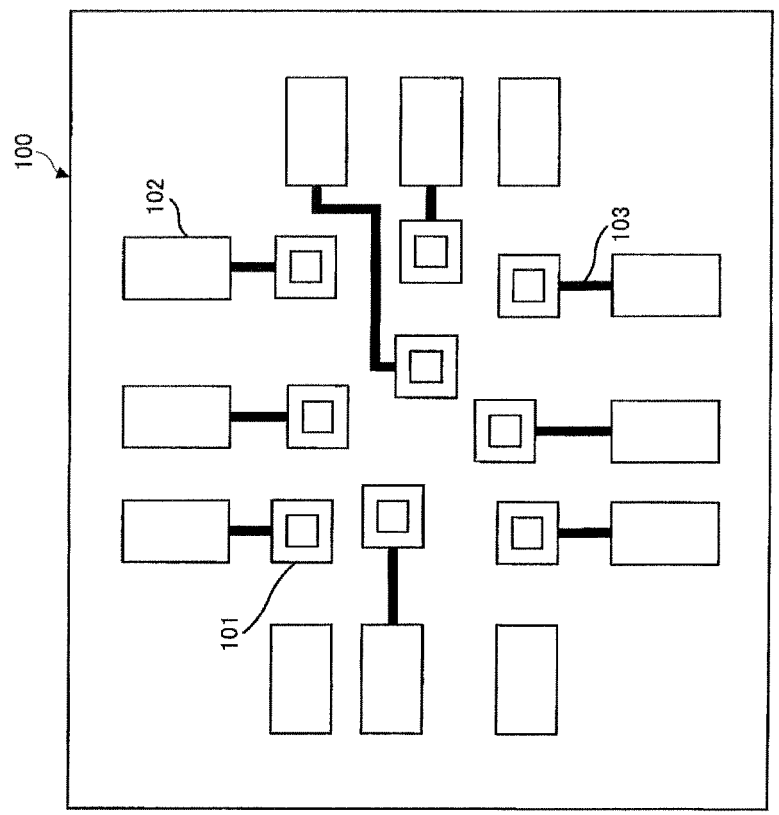
FIG. 14 illustrates a vertical cavity surface emitting laser array in which the intervals between light-emitting parts are not equal intervals.

Further, in the above-mentioned embodiment, it is also possible that the plural light-emitting parts 101 of the vertical cavity surface emitting laser array 100 are placed in such a manner that at least some of the intervals between the light-emitting parts 101 are different from the others (see FIG. 14). That is, the intervals between the adjacent light-emitting parts 101 may be different from each other.

Figure 15:
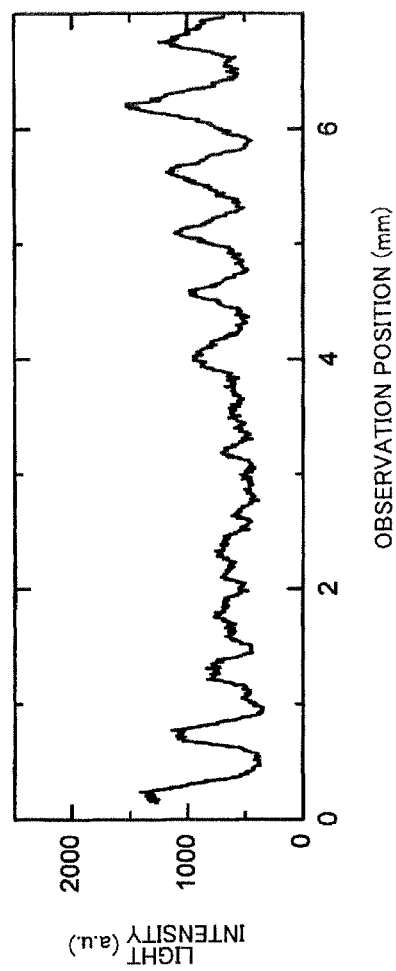
FIG. 15 illustrates a light intensity distribution of a speckle pattern when the intervals between light-emitting parts are equal intervals.

FIG. 15 shows a light intensity distribution obtained upon, in a light source including a vertical cavity surface emitting laser array in which five light-emitting parts were arranged one-dimensionally, a speckle pattern being observed by a beam profiler for a case where the intervals between the light-emitting parts were equal intervals. In this case, a periodic vibration of light intensity corresponding to the regularity of the arrangement of the light-emitting parts was identified, and the contrast ratio was 0.64.

Figure 16:
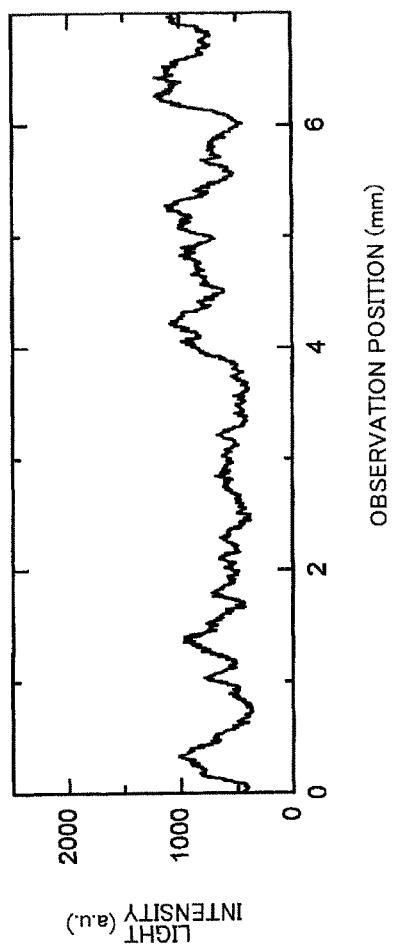
FIG. 16 illustrates a light intensity distribution of a speckle pattern when the intervals between light-emitting parts are not equal intervals.

FIG. 16 shows a light intensity distribution obtained upon, in a light source including a vertical cavity surface emitting laser array in which five light-emitting parts were arranged one-dimensionally, a speckle pattern being observed by a beam profiler for a case where the ratio between the intervals between the light-emitting parts was made irregular such as 1.0:1.9:1.3:0.7. In this case, the periodic vibration of light intensity was suppressed, and the contrast ratio was 0.56.

Thus, it is possible to further reduce the contrast ratio by making the arrangement of the plural light-emitting parts 101 in such a manner that the intervals between the plural light-emitting parts 101 are not equal intervals, whereby the regularity of a speckle pattern is disturbed.

Further, in a case where there is the possibility of erroneous paper type identification being made under the influence of disturbance light or stray light, it is also possible to increase the number of the light detection systems.

Figure 17:
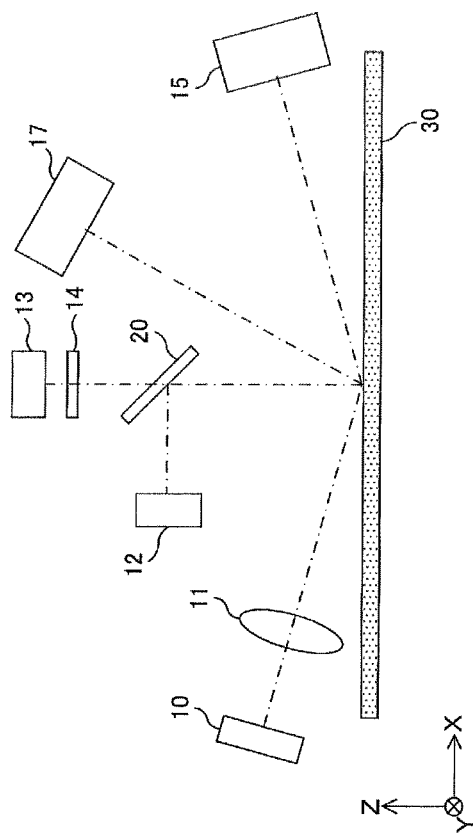
FIGS. 17 and 18 illustrate a second variant of an optical sensor.
Figure 18:
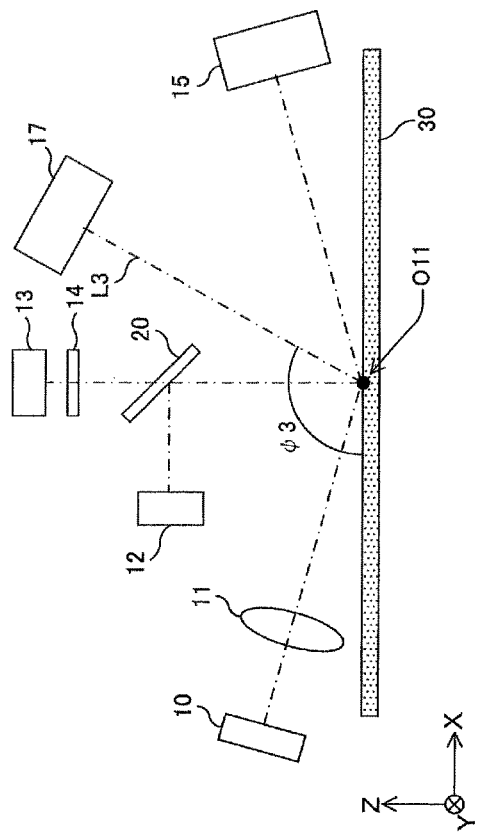

For example, as shown in FIG. 17, as a third light detection system, an optical receiver 17 may be added. The optical receiver 17 is placed at a position of receiving the surface diffusely-reflected light and the inside diffusely-reflected light. The center of the light source 10, the irradiation center O11 (see FIG. 18), the center of the polarization filter 14 and the respective centers of the optical receivers 12, 13, 15 and 17 exist on approximately the same plane. Further, the angle φ3 of the line L3 connecting the irradiation center O11 and the center of the optical receiver 17 from the surface of the sheet of recording paper 30 is 120° (see FIG. 18).

A paper type identification process carried out by the printer control device 2090 in this case will be described below. It is noted that hereinafter, "S3" denotes the signal level of the output signal of the optical receiver 17 when the light is irradiated onto the sheet of recording paper 30 from the light source 10.

(1) The plural light-emitting parts 101 of the optical sensor 2245 are caused to emit light simultaneously.

(2) The values of S1, S2 and S3 are obtained from the output signals of the respective optical receivers.

(3) The value of S3/S2 is obtained.

(4) Using a "recording paper identification table", the brand of the recording paper 30 is identified from the obtained values of S1 and S3/S2.

(5) The identified brand of the recording paper 30 is stored in the RAM, and the paper type identification process is finished.

Here, concerning plural brands of recording paper 30 that the color printer 2000 can use, the values of S1 and S3/S2 are previously measured for the respective brands of recording paper 30 during a pre-shipment process such as an adjustment process, and the measurement results are stored in the ROM of the printer control device 2090 in a form of the above-mentioned "recording paper identification table".

Figure 19:
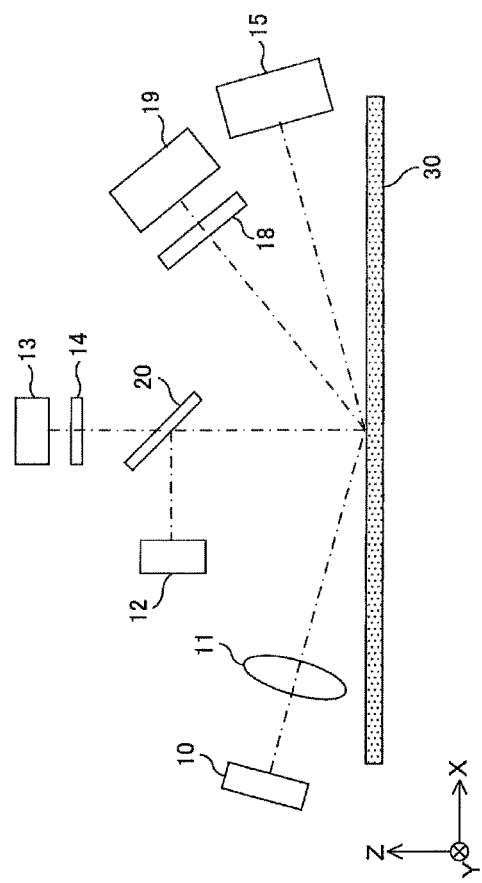
FIGS. 19 and 20 illustrate a third variant of an optical sensor.

Further, it is also possible that, for example, as shown in FIG. 19, as a third light detection system, a polarization filter 18 and an optical receiver 19 are added. The polarization filter 18 is placed on the light path of the surface diffusely-reflected light and the inside diffusely-reflected light. The polarization filter 18 transmits P-polarized light and blocks S-polarized light. The optical receiver 19 is placed on the light path of the light that has passed through the polarization filter 18. The optical receiver 19 receives the P-polarized light component of the inside diffusely-reflected light.

Figure 20:
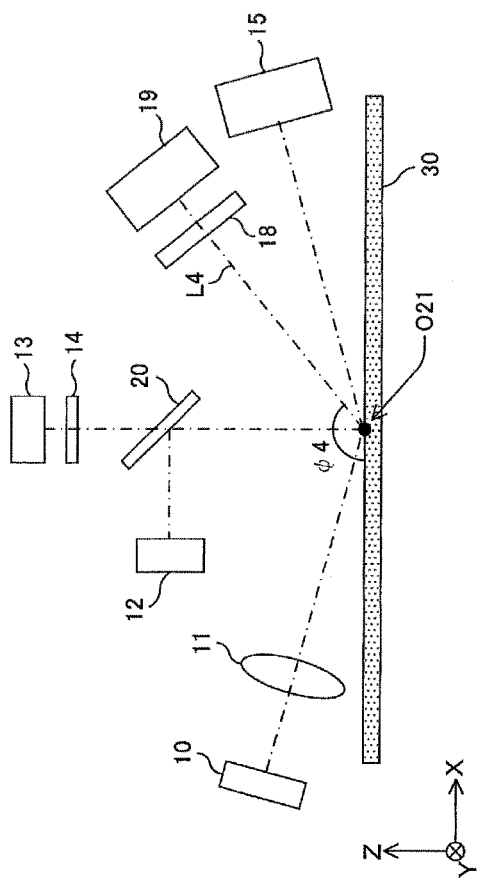

The center of the light source 10, the irradiation center O21 (see FIG. 20), the respective centers of the two polarization filters 14 and 18 and the respective centers of the optical receivers 12, 13, 15 and 19 exist on approximately the same plane. Further, the angle φ4 of the line L4 connecting the irradiation center O21 and the centers of the polarization filter 18 and the optical receiver 19 from the surface of the sheet of recording paper 30 is 150° (see FIG. 20).

A paper type identification process carried out by the printer control device 2090 in this case will be described below. It is noted that hereinafter, "S4" denotes the signal level of the output signal of the optical receiver 19 when the light is irradiated onto the sheet of recording paper from the light source 10.

(1) The plural light-emitting parts 101 of the optical sensor 2245 are caused to emit light simultaneously.

(2) The values of S1, S2 and S4 are obtained from the output signals of the respective optical receivers.

(3) The value of S4/S1 is obtained.

(4) Using a "recording paper identification table", the brand of the recording paper 30 is identified from the obtained values of S4/S1 and S2.

(5) The identified brand of the recording paper 30 is stored in the RAM, and the paper type identification process is finished.

Here, concerning plural brands of recording paper 30 that the color printer 2000 can use, the values of S4/S1 and S2 are previously measured for the respective brands of recording paper 30 during a pre-shipment process such as an adjustment process, and the measurement results are stored in the ROM of the printer control device 2090 in a form of the above-mentioned "recording paper identification table".

Figure 21:
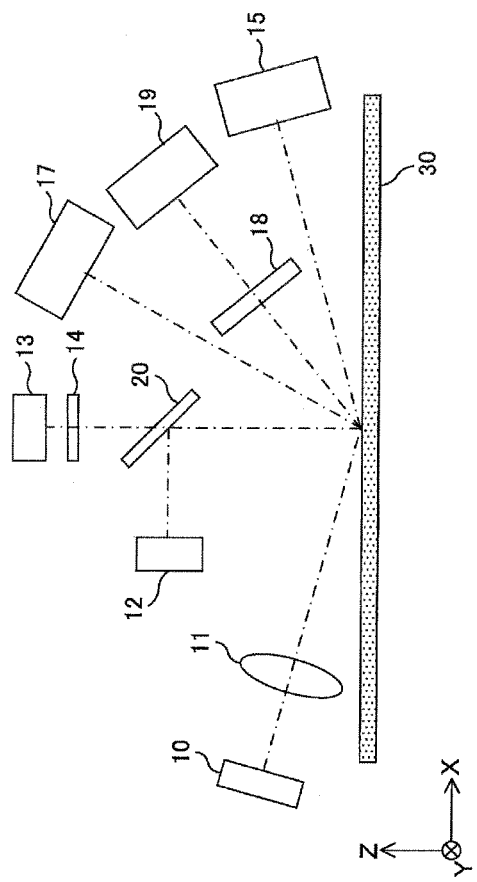
FIGS. 21 and 22 illustrate a fourth variant of an optical sensor.
Figure 22:
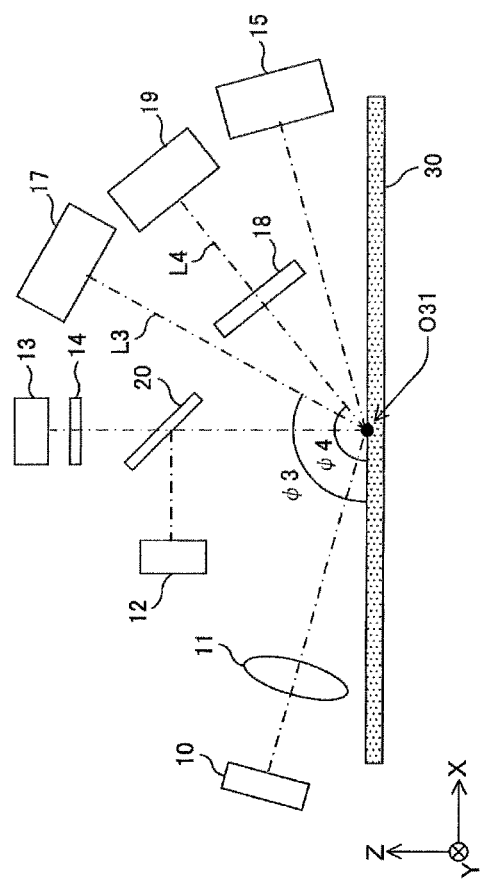

Further, it is also possible that, for example, as shown in FIGS. 21 and 22, the above-mentioned optical receiver 17, the above-mentioned polarization filter 18 and the above-mentioned optical receiver 19 are added. That is, a third light detection system including the optical receiver 17 and a fourth light detection system including the polarization filter 18 and the optical receiver 19 may be added. It is noted that in FIG. 22, "O31" denotes the irradiation center.

A paper type identification process carried out by the printer control device 2090 in this case will be described below.

(1) The plural light-emitting parts 101 of the optical sensor 2245 are caused to emit light simultaneously.

(2) The values of S1, S2, S3 and S4 are obtained from the output signals of the respective optical receivers.

(3) The values of S4/S1 and S3/S2 are obtained.

Figure 23:
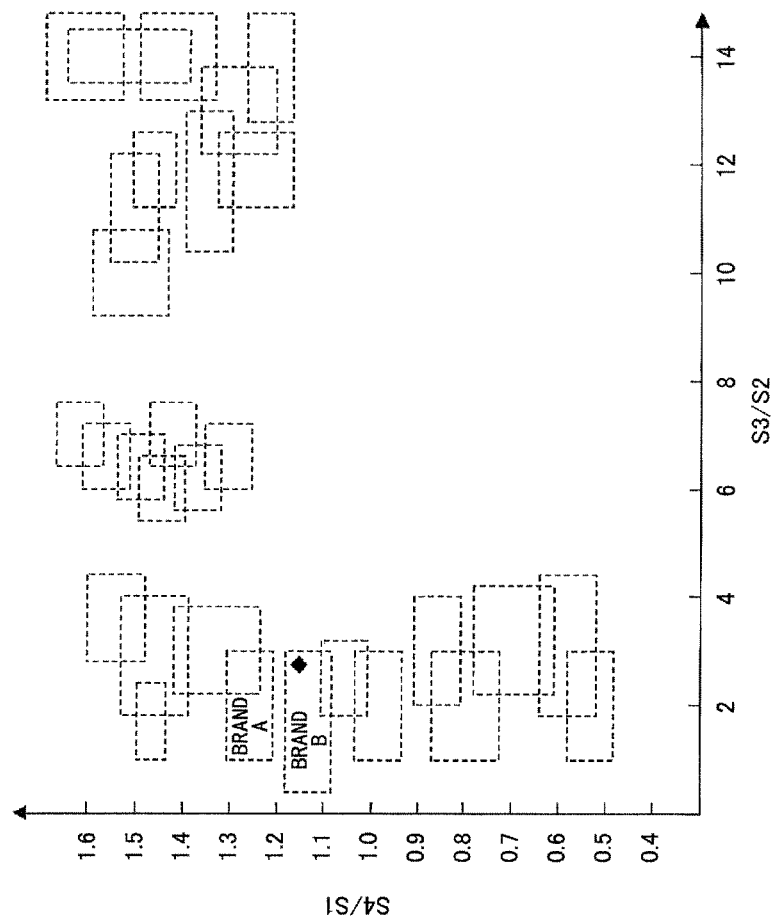
FIG. 23 illustrates a relationship of S4/S1 and S3/S2 with a brand of recording paper.

(4) Using a "recording paper identification table", the brand of the recording paper 30 is identified from the obtained values of S4/S1 and S3/S2 (see FIG. 23).

(5) The identified brand of the recording paper 30 is stored in the RAM, and the paper type identification process is finished.

Here, concerning plural brands of recording paper 30 that the color printer 2000 can use, the values of S4/S1 and S3/S2 are previously measured for the respective brands of recording paper 30 during a pre-shipment process such as an adjustment process, and the measurement results are stored in the ROM of the printer control device 2090 in a form of the above-mentioned "recording paper identification table".

It is noted that it is also possible to further add a detection system such as a detection system the same as or similar to the above-mentioned second light detection system placed on a diffusely-reflected light direction.

By thus providing the plural light detection systems for detecting diffused light reflected in mutually different directions, respectively, and identifying the sheet of recording paper 30 using calculated values such as ratios of the detected values of the respective light detection systems and so forth, it is possible to carry out the accurate identification even when disturbance light and/or stray light exist.

Further, in this case, it is also possible that the printer control device 2090 roughly narrows down paper types using S1 and S2, and then, identifies the brand of the recording paper 30 using S4/S1 and S3/S2.

In the above-mentioned example, as a method of calculation using S1 and S4, the calculation S4/S1 is used. However, the method of calculation using S1 and S4 is not limited thereto. Similarly, also the method of calculation using S2 and S3 is not limited to the calculation S3/S2.

Figure 24:
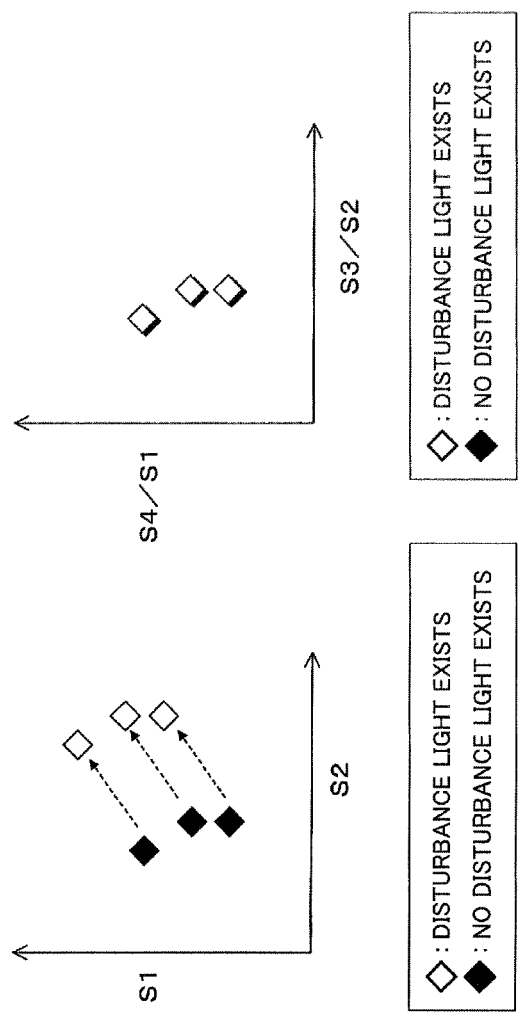
FIGS. 24A and 24B respectively illustrate influences of disturbance light.

FIGS. 24A and 24B show results of examining the impact of disturbance light in a case of paper type identification only using S1 and S2 and a case of paper type identification using S4/S1 and S3/S2. In the case of paper type identification only using S1 and S2, as shown in FIG. 24A, the detected values of the respective light detection systems increase when disturbance light exists, and there may be a possibility of erroneous paper type identification. On the other hand, in the case of paper type identification using S4/S1 and S3/S2, as shown in FIG. 24B, S4/S1 and S3/S2 hardly change even when disturbance light exists with respect to a case where disturbance light does not exist. Thus, it is possible to carry out correct paper type identification.

In this case, the above-mentioned second light detection system may include plural optical receivers. Further, the above-mentioned third or fourth light detection system may include plural polarization filters and/or plural optical receivers.

For example, in a case where the above-mentioned third light detection system includes two optical receivers, and the above-mentioned fourth light detection system includes two sets of polarization filters and optical receivers, and "S3" and "S5" denote the output levels of the respective optical receivers of the third light detection system and "S4" and "S6" denote the output levels of the respective optical receivers of the fourth light detection system, paper type identification may be carried out using the value of (S4/S1+S6/S1) and the value of (S3/S2+S5/S2). Further, it is also possible to carry out paper type identification using the value of S4/S1, the value of S6/S1, the value of S3/S2 and the value of S5/S2.

Of course, a "recording paper identification table" (such as that mentioned above) is created according to any one of these specific methods of calculation using the detected values to be used for the paper type identification, previously during a pre-shipment process such as an adjustment process, and is stored in the ROM of the printer control device 2090, in the same manner as above.

Figure 25:
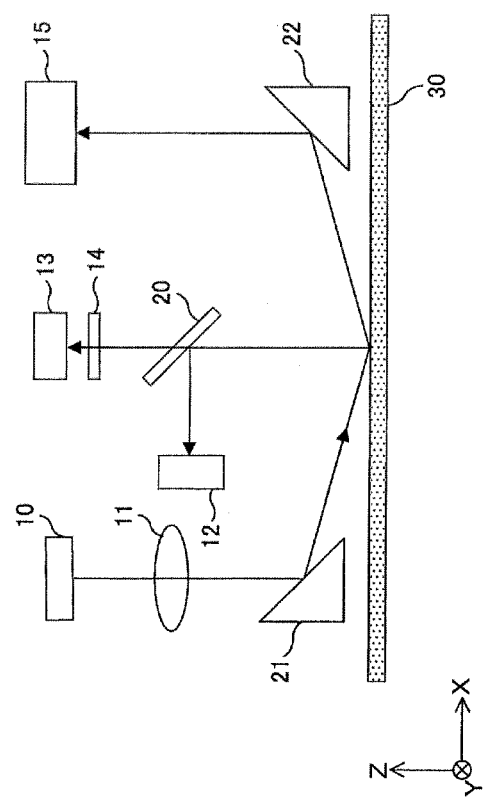
FIG. 25 illustrates a fifth variant of an optical sensor.

Further, in the above-mentioned embodiment, it is also possible that the optical sensor 2245 includes two mirrors 21 and 22 as shown in FIG. 25, for example.

Here, the light source 10 emits light in a direction parallel to the Z-axis, and the collimator lens 11 is placed in such a manner that the optical axis becomes parallel to the Z-axis.

Then, the mirror 21 bends the light path of the light that has passed through the collimator lens 11 so that it will be incident on the sheet of recording paper 30 at the incident angle of 80°.

The mirror 22 is a mirror equal to the mirror 21, and is placed at a position such that the mirror 22 faces the mirror 21 along the X-axis direction under the condition of the opening 16a existing between the mirrors 21 and 22. In this configuration, the light path of the surface specularly-reflected light from the recording paper 30 is bent by the mirror 22 so that the traveling direction will be changed to be parallel to the Z-axis.

Then, the optical receiver 15 is placed on the +Z side of the mirror 22, and receives the surface specularly-reflected light, the light path of which has been thus bent by the mirror 22.

In this case, members for supporting the light source 10, the collimator lens 11 and the optical receiver 15 in the state of being inclined are not necessary, and also, it is possible to simplify a corresponding electric circuit. Thus, it is possible to facilitate the reduction of the cost and size.

It is noted that also for a case where three or more optical receivers are provided, it is possible to facilitate miniaturization of the optical sensor 2245 by making the traveling directions of light toward the respective optical receivers be parallel to the Z-axis using mirrors.

Further, in the above-mentioned embodiment, the light source 10 has the nine light-emitting parts 101. However, the number of the light-emitting parts 101 in the light source 10 is not limited thereto.

Figure 26:
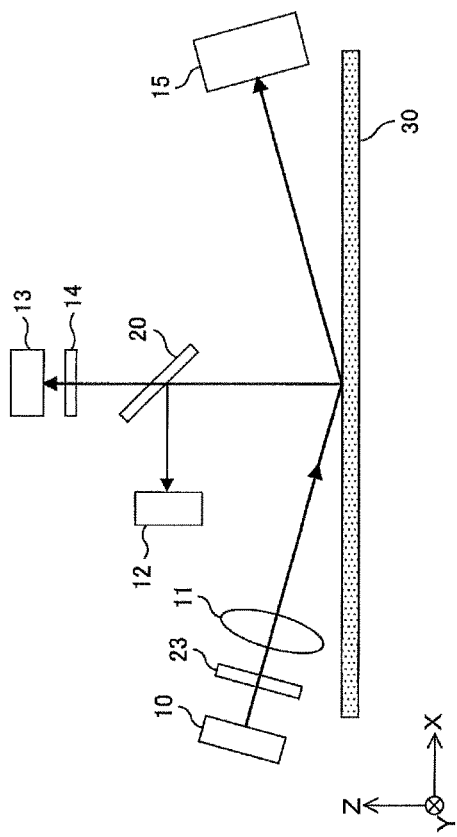
FIG. 26 illustrates a sixth variant of an optical sensor.

Further, in the above-mentioned embodiment, the linearly polarized light is emitted from the light source 10. However, the light emitted by the light source 10 is not limited thereto. However, in a case where the light source 10 is different from a light source which emits linearly polarized light, a polarization filter 23 is required as shown in FIG. 26 for making the irradiation light be S-polarized light.

Further, in the above-mentioned embodiment, it is preferable that condenser lenses are placed in front of the respective optical receivers. In this case, it is possible to reduce variations of the amounts of received light of the respective optical receivers.

In this regard, for the optical sensor 2245 for identifying the recording paper 30 based on the amounts of reflected light, reproducibility of measurement is important. In the optical sensor 2245 for identifying the recording paper 30 based on the amounts of reflected light, the measuring system is installed assuming that the measuring plane and the surface of recording paper 30 are the same plane. However, there may be a case where, due to warping, vibration or the like of the recording paper 30, the surface of recording paper 30 is inclined or floating from the measuring plain, and thus, the measuring plane and the surface of recording paper 30 are not the same plane. In this case, the amounts of reflected light may be changed, and thus, it may be difficult to stably carry out detailed identification. Below, a description will be made for specular reflection as one example.

Figure 27A:
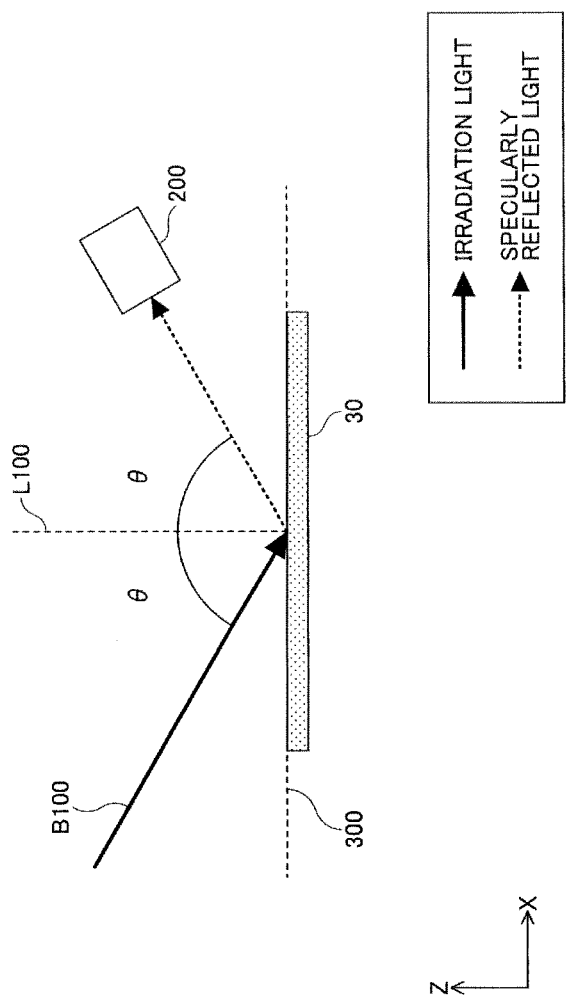
FIGS. 27A, 27B and 27C respectively illustrate changes of an amount of detected light caused by shifts between a measurement surface and a surface of recording paper.
Figure 27B:
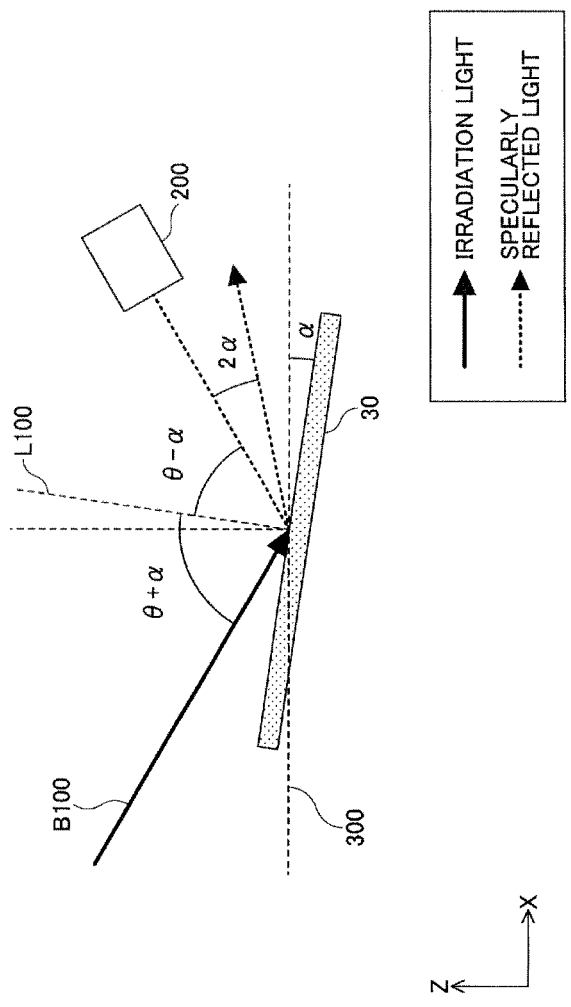
Figure 27C:
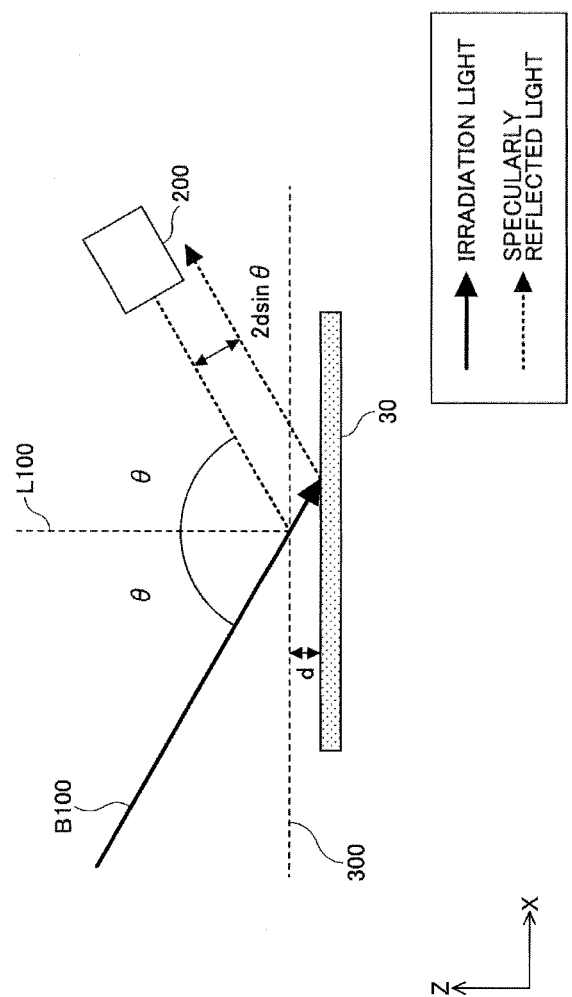

It is noted that in FIGS. 27A, 27B and 27C, L100 denotes a normal to the surface of recording paper 30. B100 denotes the irradiation light.

FIG. 27A shows a case where the measuring plane 300 and the surface of recording paper 30 are the same plane. At this time, the light detection system 200 (in the above-mentioned example, including the optical receiver 15) can receive specular-reflected light.

FIG. 27B shows a case where the surface of recording paper 30 is inclined from the measuring plane 300 by the angle α. At this time, when the positional relationship between the irradiation system (not shown in FIGS. 27A to 27C) and the light detection system 200 is the same as the case of FIG. 27A, the light detection system 200 receives the light in a direction shifted from the specularly-reflected direction by 2α. The intensity distribution of reflected light is moved as the reception direction is thus shifted. Thus, the light detection system 200 receives the light at a position shifted from the position receiving the specularly-reflected light by "L×tan 2α". It is noted that "L" denotes the distance between the central position of the irradiation area and the light detection system 200. Further, the actual incident angle is shifted from the prescribed incident angle θ by α, and the reflectance from the recording paper 30 is changed. Therefore, the amount of detected light is changed, and consequently, it is difficult to carry out detailed identification.

FIG. 27C shows a case where the surface of recording paper 30 is shifted from the measuring plane 300 in a height direction (Z-axis direction) by "d". At this time, when the positional relationship between the irradiation system and the light detection system 200 is the same as the case of FIG. 27A, since the intensity distribution of reflected light is moved as the recording paper 30 is thus shifted, the light detection system 200 receives the light at a position shifted from the position receiving the specularly-reflected light by "2d×sin θ". Therefore, the amount of detected light is changed, and consequently, it is difficult to carry out detailed identification.

The cases of FIGS. 27B and 27C can be dealt with by placing a condenser lens in front of the light detection system 200 in consideration of the moving amount of the intensity distribution of reflected light, and thereby collecting the light even when the intensity distribution of reflected light is moved, so that the light detection system 200 can positively receive the specularly-reflected light.

Further, it is also possible to eliminate the inconvenience caused by the case where the surface of the sheet of recording paper 30 is not the same as the measuring plane 300, by using a photodiode (PD) having a wide light receiving area as the optical receiver, or reducing the beam diameter of the irradiation light.

Further, it is also possible to obtain a sufficiently wide light receiving area in consideration of the moving amount of the intensity distribution of reflected light, by using an array of PDs as the optical receiver. In this case, even when the intensity distribution of reflected light has been moved, it is possible use the maximum signal from among the signals detected by the respective PDs as the signal of the specularly-reflected light. In a case of using such an array of PDs, by reducing the light receiving areas of the respective PDs, it is possible to reduce a variation of the output caused by a shift of the specularly-reflected light from the center of the light receiving area. Thus, it is possible to carry out the detection more precisely.

Here, for the sake of convenience, the description has been made for specularly-reflected light. A change of the amount of detected light caused by a difference between the measuring plane and the surface of recording paper 30 may also occur for surface diffusely-reflected light or inside diffusely-reflected light. Also such a case can be dealt with in the same way as the case of specularly-reflected light described above.

By using the optical sensors according to the embodiments, it is possible to identify an object in detail without much increasing the cost and size.

Thus, the optical sensors and image forming apparatuses have been described by the embodiments. However, the present invention is not limited to these specifically disclosed embodiments, and variations and modifications may be made without departing from the scope of the present invention.

For example, in the above-mentioned embodiment, it is also possible to provide a processing device in the optical sensor 2245, and part of the processing carried out by the printer control device 2090 may be carried out by the processing device.

Further, in the above-mentioned embodiment, the single paper supply tray 2060 is provided. However, the number of paper supply trays is not limited thereto, and plural paper supply trays may be provided. In this case, the optical sensors 2245 may be provided for the respective paper supply trays.

Further, in the above-mentioned embodiment, it is also possible that the brand of recording paper 30 is identified while the recording paper 30 is being conveyed. In this case, the optical sensor 2245 is placed near the paper conveyance path. For example, the optical sensor 2245 may be placed near the paper conveyance path between the paper supply roller 2054 and the transfer roller 2042.

Further, an object to be identified by the optical sensor 2245 is not limited to recording paper 30.

Further, the above-mentioned embodiment has been described for the case of the color printer 2000 as an image forming apparatus. However, an image forming apparatus to which the present invention is applied is not limited thereto. For example, an image forming apparatus to which the present invention is applied may be a laser printer that forms a monochrome image. Further, an image forming apparatus to which the present invention is applied may be an image forming apparatus other than a printer, i.e., for example, a copier, a facsimile machine, or a multifunction peripheral (MFP) having the respective functions of these apparatuses.

Further, the above-mentioned embodiment has been described for the case where the image forming apparatus has the four photosensitive member drums 2030*a* to 2030*d*. However, the number of photosensitive member drums is not limited thereto. For example, an image forming apparatus to which the present invention is applied may be a printer having five photosensitive member drums.

Further, according to the above-mentioned embodiment, in the image forming apparatus, the toner image is transferred from the photosensitive member drum to the recording paper via the transfer belt 2040. However, the type of an image forming apparatus to which the present invention is applied is not limited thereto. An image forming apparatus to which the present invention is applied may be an image forming apparatus in which a toner image is directly transferred to a sheet of recording paper from a photosensitive member drum.

Further, the optical sensor 2245 may also be applied to an image forming apparatus in which an image is formed as a result of ink being discharged onto a sheet of recording paper.

Figure 28:
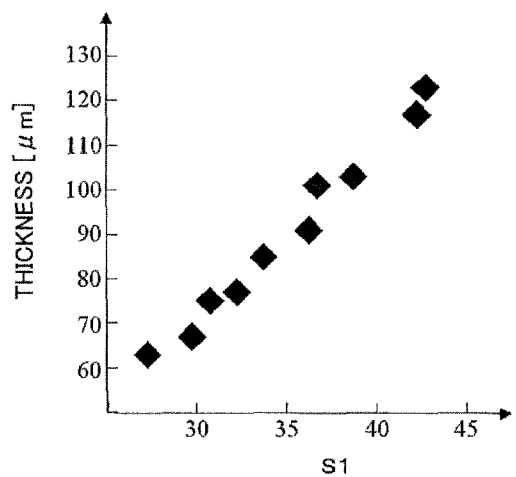
FIG. 28 illustrates a relationship between a thickness and S1.

Further, it is possible to apply the optical sensor 2245 to detection of the thickness of an object (see FIG. 28). In the related art, a thickness sensor has a reflective configuration, and thus, it is necessary to place optical systems on both sides of an object that is inserted therebetween. For this purpose, a supporting member(s) or the like is required. In contrast thereto, the optical sensor 2245 detects the thickness only using reflected light. Thus, the optical system should be placed only on one side of the object. Thus, it is possible to reduce the number of required parts/components, and it is possible to reduce the cost and size. Further, the optical sensor 2245 for detecting the thickness of an object is most suitable to be installed in an image forming apparatus that requires detection of the thickness of the object.

Figure 29:
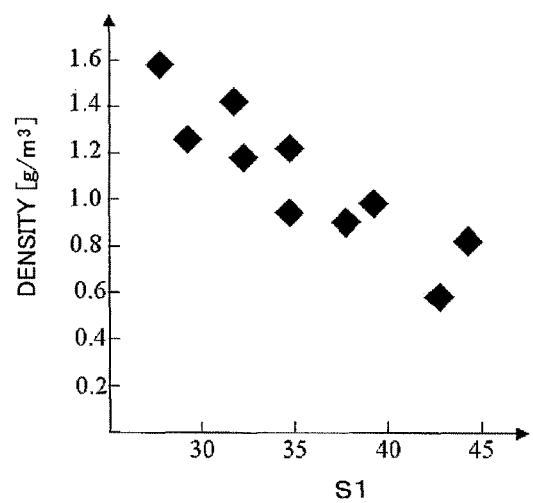
FIG. 29 illustrates a relationship between a density and S1.

Further, it is possible to apply the optical sensor 2245 to detection of the density of an object (see FIG. 29). In the related art, a density sensor has a reflective configuration, and thus, it is necessary to place optical systems on both sides of an object that is inserted therebetween. For this purpose, a supporting member(s) or the like is required. In contrast thereto, the optical sensor 2245 detects the density only using reflected light. Thus, the optical system should be placed only on one side of the object. Thus, it is possible to reduce the number of required parts/components, and it is possible to reduce the cost and size. Further, the optical sensor 2245 for detecting the density of an object is most suitable to be installed in an image forming apparatus that requires detection of the density of the object.

The present application is based on Japanese priority application No. 2012-044930 filed on Mar. 1, 2012, the entire contents of which are hereby incorporated herein by reference.

What is claimed is:

1. An optical sensor comprising:
   an irradiation system that emits linearly polarized light of a first polarization direction toward a surface of an object from an incident direction inclined with respect to a normal to the surface, scattering occurring inside the object;
   a first light detection system that includes a first light detector placed on a light path of light emitted from the irradiation system and specularly reflected by the object;
   a second light detection system that includes
      a separation optical element placed on a light path of light diffusely reflected by the object, on a plane of incidence of the object, and extracting a linearly polarized light component of the first polarization direction included in the light diffusely reflected by the object,
      a second light detector receiving the linearly polarized light component of the first polarization direction extracted by the separation optical element, and
      a third light detector receiving a light portion of light diffusely reflected by the object and inside diffusely-reflected light, the inside diffusely-reflected light including a light component of the first polarization direction and a light component of a second direction orthogonal to the first polarization direction; and
   a control device that determines a quantity of the inside diffusely-reflected light based on an output signal from the third light detector and an output signal from the second light detector.

2. The optical sensor as claimed in claim 1, wherein the second light detection system includes a dividing optical element that divides the light diffusely reflected by the object into one light and another light, and the separation optical element is placed on a light path of the one light, and the third light detector is placed on a light path of the another light.

3. The optical sensor as claimed in claim 2, wherein the dividing optical element is placed on a light path of light that is diffusely reflected in a direction of a normal to the surface of the object.

4. The optical sensor as claimed in claim 1, further comprising:
   a third light detection system that includes at least one light detector placed on a light path diffusely reflected by the object, on the plane of incidence of the object; and
   a processing part that identifies the object based on outputs of the respective light detectors of the second light detection system and a ratio between outputs of the at least one light detector of the third light detection system and the first light detector.

5. The optical sensor as claimed in claim 1, wherein the irradiation system includes a vertical cavity surface emitting laser array having plural light-emitting parts that are two-dimensionally arranged.

6. An image forming apparatus which forms an image on a recording medium, comprising:
   the optical sensor claimed in claim 1 in which the object is the recording medium; and
   an adjustment device that identifies a brand of the recording medium based on output of the optical sensor and adjusts image forming conditions according to the identified brand.

7. The optical sensor as claimed in claim 1, further comprising:
   a third light detection system that includes a light detector receiving light diffusely reflected in a direction different from the light respectively received by the first and second light detection systems.

8. An optical sensor comprising:
   an irradiation system that emits linearly polarized light of a first polarization direction toward a surface of an object from an incident direction inclined with respect to a normal to the surface, scattering occurring inside the object;

a first light detection system that includes a first light detector placed on a light path of light emitted from the irradiation system and specularly reflected by the object; and a second light detection system that includes
- a separation optical element placed on a light path of light diffusely reflected by the object, on a plane of incidence of the object, and extracting a linearly polarized light component of the first polarization direction included in the light diffusely reflected by the object,
- a second light detector receiving the linearly polarized light component of the first polarization direction extracted by the separation optical element, and
- a third light detector receiving a light portion of light diffusely reflected by the object and inside diffusely-reflected light, the inside diffusely-reflected light including a light component of the first polarization direction and a light component of a second direction orthogonal to the first polarization direction;

a third light detection system that includes
- at least one polarization optical element placed on a light path of light diffusely reflected by the object, on the plane of incidence of the object, and transmitting linearly polarized light of a second polarization direction that is orthogonal to the first polarization direction, and
- at least one light detector receiving light that has passed through the at least one polarization optical element; and a processing part that identifies the object based on output of the first light detector and a ratio between output of the at least one light detector of the third light detection system and a difference between outputs of the two light detectors of the second light detection system.

9. An optical sensor comprising:

an irradiation system that emits linearly polarized light of a first polarization direction toward a surface of an object from an incident direction inclined with respect to a normal to the surface, scattering occurring inside the object;

a first light detection system that includes a first light detector placed on a light path of light emitted from the irradiation system and specularly reflected by the object; and a second light detection system that includes
- a separation optical element placed on a light path of light diffusely reflected by the object, on a plane of incidence of the object, and extracting a linearly polarized light component of the first polarization direction included in the light diffusely reflected by the object,
- a second light detector receiving the linearly polarized light component of the first polarization direction extracted by the separation optical element, and
- a third light detector receiving a light portion of light diffusely reflected by the object and inside diffusely-reflected light, the inside diffusely-reflected light including a light component of the first polarization direction and a light component of a second direction orthogonal to the first polarization direction;

a third light detection system that includes at least one light detector placed on a light path of light diffusely reflected by the object, on the plane of incidence of the object;

a fourth light detection system that includes
- at least one polarization optical element placed on a light path of light diffusely reflected by the object, on the plane of incidence of the object, and transmitting linearly polarized light of a second polarization direction that is orthogonal to the first polarization direction, and
- at least one light detector receiving light that has passed through the at least one polarization optical element; and a processing part that identifies the object based on a ratio between outputs of the at least one light detector of the third light detection system and the first light detector, and a ratio between output of the at least one light detector of the fourth light detection system and a difference between outputs of the two light detectors of the second light detection system.

* * * * *